US012721795B2

(12) United States Patent
Hug et al.

(10) Patent No.: US 12,721,795 B2
(45) Date of Patent: Sep. 1, 2026

(54) PERSONAL DENTAL CARE PRODUCT FOR PREVENTING DEMINERALISATION

(71) Applicant: CREDENTIS AG, Windisch (CH)

(72) Inventors: Michael Hug, Zofingen (CH); Dominikus Amadeus Lysek, Windisch (CH)

(73) Assignee: Credentis AG, Windisch (CH)

(*) Notice: Subject to any disclaimer, the term of this patent is extended or adjusted under 35 U.S.C. 154(b) by 1026 days.

(21) Appl. No.: 17/755,410

(22) PCT Filed: Dec. 4, 2020

(86) PCT No.: PCT/EP2020/084650

§ 371 (c)(1),
(2) Date: Apr. 28, 2022

(87) PCT Pub. No.: WO2021/110923

PCT Pub. Date: Jun. 10, 2021

(65) Prior Publication Data

US 2022/0387269 A1 Dec. 8, 2022

(30) Foreign Application Priority Data

Dec. 4, 2019 (EP) .................................... 19213470

(51) Int. Cl.

*A61K 8/19* (2006.01)
*A61K 8/24* (2006.01)
*A61K 8/34* (2006.01)
*A61K 8/64* (2006.01)
*A61Q 11/00* (2006.01)

(52) U.S. Cl.

CPC .................. *A61K 8/19* (2013.01); *A61K 8/24* (2013.01); *A61K 8/345* (2013.01); *A61K 8/645* (2013.01); *A61Q 11/00* (2013.01); *A61K 2800/92* (2013.01)

(58) Field of Classification Search

CPC ................................. A61K 8/64; A61Q 11/00
USPC .................................................. 424/49, 215
IPC .................................................... A61Q 11/00
See application file for complete search history.

(56) References Cited

U.S. PATENT DOCUMENTS

| | | | | |
|---|---|---|---|---|
| 6,548,630 | B1 | 4/2003 | Zhang et al. | |
| 9,511,021 | B2 | 12/2016 | Rudolph et al. | |
| 9,809,633 | B2 * | 11/2017 | Sarikaya | A61K 8/64 |
| 2008/0199431 | A1 | 8/2008 | Capito et al. | |
| 2016/0199283 | A1 * | 7/2016 | Hug | A61Q 11/00 132/321 |

FOREIGN PATENT DOCUMENTS

| | | | |
|---|---|---|---|
| EP | 1495680 | A1 | 1/2005 |
| EP | 2327428 | A2 | 6/2011 |
| EP | 2853256 | A1 | 1/2015 |
| EP | 3248590 | A1 | 11/2017 |
| EP | 3284477 | A1 | 2/2018 |
| GB | 2496654 | A | 5/2013 |
| NO | 2014/152952 | A1 | 9/2014 |
| RU | 2677231 | C1 | 1/2019 |
| WO | 2004/007532 | A2 | 1/2004 |
| WO | 2006/047315 | A2 | 5/2006 |
| WO | 2006/073889 | A2 | 7/2006 |
| WO | 2006/127559 | A2 | 11/2006 |
| WO | 2007/000979 | A1 | 4/2007 |
| WO | 2007/143989 | A1 | 12/2007 |
| WO | 2008/113030 | A2 | 9/2008 |
| WO | 2009/026729 | A1 | 3/2009 |
| WO | 2009/100276 | A2 | 8/2009 |
| WO | 2010/019651 | A1 | 2/2010 |
| WO | 2010/041636 | A1 | 4/2010 |
| WO | 2010/103887 | A1 | 9/2010 |
| WO | 2011/106619 | A2 | 9/2011 |
| WO | 2013/050432 | A2 | 4/2013 |
| WO | 2014/027012 | A1 | 2/2014 |

(Continued)

OTHER PUBLICATIONS

Kirkham et al., "Self-assembling Peptide Scaffolds Promote Enamel Remineralization." Journal of Dental Research, vol. 86, Issue 5, May 2007, pp. 426-430. (Year: 2007).*

(Continued)

*Primary Examiner* — Walter E Webb
(74) *Attorney, Agent, or Firm* — Pabst Patent Group LLP

(57) ABSTRACT

The present invention provides new dental care products comprising self-assembling peptides that are capable of undergoing self-assembly at a certain pH that are useful in dental care, in particular, useful for reducing or preventing demineralisation of teeth of a subject, in particular, for reducing or preventing further demineralisation of teeth of a subject. The dental care products comprises self-assembling peptides, in particular, comprise self-assembling peptides comprising the sequence of SEQ ID NO: 21, that are capable of undergoing self-assembly at a pH below 7.5, wherein the self-assembling peptides are essentially present in the dental care product in assembled form, and a pharmaceutically acceptable basis. The dental care product is an essentially solid product selected from the group consisting of chewing gum, soft chew, toffee, gelatin gum, chewy candy, chew toy, lozenge. Preferably, it is a chewy product. The dental care product is not abrasive. The dental care product is useful for reducing or preventing (further) demineralisation of a tooth surface of a subject with demineralised teeth, e.g., or a subject with xerostomia, hyopsalivation, bruxism, gastroesophageal reflux disease, dentine hypersensitivity and/or tooth erosion. Preferably, it is also useful for cleaning the tooth surface. Products of the invention are useful for animals and humans. The invention also provides a process for preparing the dental care products of the invention. The invention enables non-targeted treatment of a plurality of teeth, and it is independent of the diagnosis of caries.

15 Claims, 11 Drawing Sheets

Specification includes a Sequence Listing.

(56) References Cited

FOREIGN PATENT DOCUMENTS

| | | | |
|---|---|---|---|
| WO | 2014/142952 | A1 | 9/2014 |
| WO | 2014/167310 | A1 | 10/2014 |
| WO | 2015/044268 | A1 | 4/2015 |
| WO | 2017/202940 | A1 | 11/2017 |
| WO | 2017/202943 | A1 | 11/2017 |

OTHER PUBLICATIONS

Office Action issued by Russian Patent Office, RU Patent App. 2022117761/04, issued Sep. 9, 2024.
Aggeli, Amalia, et al., "pH as a Trigger of Peptide B-Sheet Self-Assembly and Reversible Switching between Nematic and Isotropic Phases," Journal of American Chemical Society, vol. 125 (2003), pp. 9619-9628.
Andersson, Lars, et al., "Large-Scale Synthesis of Peptides," Biopolymdes (Peptide Science), vol. 55 (2000), pp. 227-250.
Arifa, Mando K., et al., "Recent Advances in Dental Hard Tissue Remineralization: a Review of Literature," International Journal of Clinical Pediatric Dentistry, vol. 12, Issue 2 (2019), pp. 139-144.
Aslani, Abolfazl, et al., "Design, formulation and evaluation of caffeine chewing gum," Advanced Biomedical Research, vol. 2, Issue 3 (2013) (7 pages).
Brunton, P. A., et al., "Treatment of early caries lesions using biomimetic self-assembling peptides—a clinical safety trial," British Dental Journal, vol. E6 (2013) (6 pages).
Carrick, Lisa M., et al., "Effect of ionic strength on the self-assembly, morphology and gelation of pH responsive B-sheet tape-forming peptides," Setrahedron, vol. 63 (2007), pp. 7457-7467.
Chaudhary, Shivang A., et al., "Directly compressible medicated chewing gum formulation for quick relief from common cold," International Journal of Pharmaceutical Investigation, vol. 2, Issue 3 (2012), pp. 123-133.
Dewsbury, Diana M. A, et al., "A complete cross-over design evaluating canine acceptance of Carprieve® and Rimadyl® carprofen chewable tablets in healthy dogs," BMC Veterinary Research, vol. 15 (2019) (8 pages).
Fasoulas, Aristeidis, et al., "Detection of dental plaque with disclosing agents in the context of preventive oral hygeiene training programs," Heliyon, vol. 5 (2019) (9 pages).
Jablonski-Momeni, A., et al., "Randomized in situ clinical trial investigating self-assembling peptide matrix P11-4 in the prevention of artificial caries lesions," Scientific Reports, vol. 9 (2019) (10 pages).
Jagdale, Swati, et al., "Formulation and evaluation of chewable tablet of levamisole," Int. J. Res. Pharm. Sci., vol. 1, Issue 3 (2010), pp. 282-289.
Kind, L., et al., "Biomimetric Remineralization of Carious Lesions by Self-Assembling Peptide," Journal of Dental Research, I-8 (2017) (8 pages).
Kirkham, J., et al., "Self-assembling Peptide Scaffolds Pormote Enamel Remineralization," Journal of Dental Research, vol. 86, No. 5 (2007), pp. 426-430.
Kyle, Stuart, et al., "Production of self-assembling biomaterials for tissue engineering," Trends Biotechnology, vol. 27, No. 7 (2009), pp. 423-433.
Kyle, Stuart, et al., "Recombinant self-assembling peptides as biomaterials for tissue engineering," Biomaterials, vol. 31 (2010), pp. 9395-9405.
Larsen, M. J., et al., "Enamel Erosion by Some Soft Drinks and Orange Juices Relative to Their pH, Buffering Effect and Contents of Calcium Phosphate," Caries Res., vol. 33 (1999), pp. 81-87.
Merrifield, R. B., et al., "Solid Phase Peptide Synthesis. I. The Synthesis of a Tetrapeptide," Rockefeller Insitute, vol. 85 (1963), pp. 2149-2154.
Roa, Arathi, et al., "The Role of Remineralizing Agents in Dentistry: a Review," Compendium, vol. 32, No. 6 (2011), pp. 26-34.
Schlee, Markus, et al., "Self-assembling peptide matrix for treatment of dentin hypersensitivity: a randomized controlled clinical trial," Journal of Periodontology, (2018) (8 pages).
Schlee, M., et al., "Klinischer Effekt biomimetischer Mineralisation bei Approximalkaries," Stomatologie, vol. 4 (2014) (7 pages).
Soares, Renita, et al., Assessment of Enamel Remineralisation After Treatment with Four Different Remineralising Agents: a Scanning Eletron Microscopy (SEM) Study, Journal of Clinical and Diagnostic Research, vol. 11, No. 4 (2017), pp. 136-141.
Umashankar, M. S., et al., "Chewable Lozenge Formulation—a Review," International Research Journal of Pharmacy, vol. 7, No. 4 (2016) (9 pages).
Zumbe, Albert, et al., "Polyols in confectionery: the route to sugar-free, reduced sugar and reduced calorie confectionery," British Journal of Nutrition, vol. 85 (2001),k pp. S31-S45.
International Search Report and Written Opinion, PCT/EP2020/084650, mailed May 7, 2021 (13 pages).
Office Action and Search Report issued by Russian Patent Office, RU Patent App. 2022117761/04, issued Apr. 23, 2024.
Klimuszko, Elzbieta, et al., "Evaluation of calcium and magnesium contents in tooth enamel without any pathological changes: in vitro preliminary study," Odontology, vol. 106 (2018), pp. 369-376.

* cited by examiner 200 nm 200 nm

A

| | |
|---|---|
| Original Surface-varnish protected **"V"** | Sample 1- polymerized **"P"** |
| Sample 2- monomerized **"M"** | Unprotected **"C"** |

B

C

D

E

F

G

PERSONAL DENTAL CARE PRODUCT FOR PREVENTING DEMINERALISATION

The present invention provides new dental care products comprising self-assembling peptides that are capable of undergoing self-assembly at a certain pH that are useful in dental care, in particular, useful for reducing or preventing demineralisation of teeth of a subject, in particular, for reducing or preventing further demineralisation of teeth of a subject. The dental care product comprises self-assembling peptides, in particular, comprise self-assembling peptides comprising the sequence of SEQ ID NO: 21, which are capable of undergoing self-assembly at a pH below 7.5, wherein the self-assembling peptides are essentially present in the dental care product in assembled form, and a pharmaceutically acceptable basis. The dental care product is an essentially solid product selected from the group consisting of chewing gum, soft chew, toffee, gelatin gum, chewy candy, chew toy, marshmallow, lozenge, or tablet. Preferably, it is a chewy product. The dental care product is not abrasive. The dental care product is useful for reducing or preventing (further) demineralisation of a tooth surface of a subject with demineralised teeth, e.g., or a subject with xerostomia, hyopsalivation, bruxism, gastroesophageal reflux disease, dentine hypersensitivity and/or tooth erosion. Preferably, in these diseases, a layer of self-assembling peptides forms on the tooth surface which may be eroded or demineralized, i.e., which acts as a sacrificial layer before the tooth itself can be damaged. Preferably, the dental care product of the invention is also useful for cleaning the tooth surface. Products of the invention are useful for animals and humans. The invention also provides a process for preparing the dental care products of the invention. The invention enables non-targeted treatment of a plurality of teeth, and it is independent of the diagnosis of caries.

Demineralization of teeth is the removal of minerals (mainly calcium and phosphate) from any of the hard tissues: enamel, dentine, and cementum. It begins at the surface, and may progress into development of cavities unless arrested or reversed by remineralisation.

Demineralization is caused by bacteria excreting acids as a product of their metabolism of carbohydrates. By reducing the intake frequency of carbohydrates in an individual's diet, remineralization can be increased and demineralization decreased. A loss of the tooth enamel structure and cavitation may occur if the demineralization phase continues to outweigh the remineralization phase over a long period of time. This disturbance of the remineralization/demineralization equilibrium caused by the presence of fermentable carbohydrates continues until the saliva has returned to a normal pH and had sufficient time to penetrate and neutralize the acids within any cariogenic biofilm present (Arathi Rao, et al. 2011. The Role of Remineralizing Agents in dentistry: A Review. Volume 32, Number 6; Wikipedia on Remineralisation_of_teeth#Treatment_and_prevention).

In addition to bacterial invasion, enamel is also susceptible to other destructive forces. Bruxism, also known as clenching of or grinding on teeth, destroys enamel very quickly. The wear rate of enamel, called attrition, is 8 micrometers a year from normal factors. A common misconception is that enamel wears away mostly from chewing, but actually teeth rarely touch during normal chewing. Furthermore, normal tooth contact is compensated physiologically by the periodontal ligaments and the arrangement of dental occlusion. The truly destructive forces are the parafunctional movements, as found in bruxism, which can cause irreversible damage to the enamel.

Other nonbacterial processes of enamel destruction include abrasion (involving foreign elements, such as toothbrushes), erosion (involving chemical processes, such as dissolving by soft drinks or lemon and other juices (Larsen M J et al. 1999. Enamel erosion by some soft drinks and orange juices relative to their pH, buffering effect and contents of calcium phosphate. Caries Res. 33 (1): 81-87), and possibly abfraction (involving compressive and tensile forces). Gastroesophageal reflux disease can also lead to erosive enamel loss, as acid refluxes up the esophagus and into the mouth, occurring most during overnight sleep. (Wikipedia on Tooth_enamel#Enamel_loss).

Acid erosion is a type of tooth wear. It is defined as the irreversible loss of tooth structure due to chemical dissolution by acids not of bacterial origin. Dental erosion is the most common chronic disease of children ages 5-17, although it is only relatively recently that it has been recognized as a dental health problem. There is generally widespread ignorance of the damaging effects of acid erosion; this is particularly the case with erosion due to fruit juices because they tend to be seen as healthy. Acid erosion begins in the enamel, causing it to become thin, and can progress into dentin, giving the tooth a dull yellow appearance and leading to dentin hypersensitivity.

The most common cause of erosion is by acidic foods and drinks. In general, foods and drinks with a pH below 5.0-5.7 have been known to trigger dental erosion effects. Numerous clinical and laboratory reports link erosion to excessive consumption of drinks. Those thought to pose a risk are soft drinks, some alcohol and fruit drinks, fruit juices such as orange juice (which contain citric acid) and carbonated drinks such as colas (in which the carbonic acid is not the cause of erosion, but citric and phosphoric acid). Additionally, wine has been shown to erode teeth, with the pH of wine as low as 3.0-3.8. Other possible sources of erosive acids are from exposure to chlorinated swimming pool water, and regurgitation of gastric acids. In children with chronic diseases, the use of medicines with acid components is a risk factor too. Dental erosion has also been recorded in the fossil record and was likely caused by the consumption of acidic fruits or plants. (Wikipedia on Acid Erosion).

To prevent demineralisation in the mouth, it is important for an individual to ensure they have a well-balanced diet, including foods containing calcium and foods that are low in acids and sugars. Fluoride is also believed to prevent demineralisation, as incorporation of fluoride into enamel leads to fluoridated hydroxyapatite which has an improved resistance to acids. Fluoride may be administered in dental care products such as toothpaste, or in food or drinks, e.g., in some regions, it is added to drinking water.

In a healthy subject, there is a balance of demineralisation and remineralisation that maintains health of the teeth. There are therefore many strategies to counter demineralisation that are based on increasing remineralisation of teeth.

To date, tooth remineralisation is achieved mainly by the delivery of either fluoride or calcium and phosphate ions onto tooth lesions or cavities (Arifa et al., Int J Clin Pediatr Dent 12(2): 139-144). The calcium and phosphate ions are usually included in toothpastes, which also contain e.g. abrasives, fluorides, surfactants and other remineralisation agents. The calcium and phosphate ions may be used in various crystalline forms, e.g. as hydroxyapatite-based materials, or as amorphous calcium phosphate, such as in some casein phosphopeptide-based materials. For example, WO 2013/050432 describes such remineralising agents and options for contacting the mucosa with these agents. WO 2009/100276 teaches a dental floss associated with a basic amino acid in free or salt form, e.g., for promoting remineralization.

More recently, an alternative approach to tooth remineralisation has been described, which is based on short rationally designed self-assembling peptides. WO 2004/007532 discloses peptides that are capable of forming three-dimensional scaffolds, thereby promoting nucleation of de-novo calcium phosphate. These artificial peptides assemble to form beta-sheet, tape-like assemblies. The peptide assemblies can switch from a fluid to a nematic, stiffer gel state in response to chemical or physical triggers. The peptides were designed to form assemblies in response to certain pH and/or ionic strength in the following hierarchical order: tapes, ribbons, fibrils and fibres. Aggeli et al. (2003, J. Am. Chem. Soc. 125, 9619-9628) analyse pH as a trigger of peptide beta-sheet self-assembly.

Several other self-assembling peptides have been described in the prior art. For example, WO 2010/041636 A1 describes a bioadsorbable peptide tissue occluding agent containing an artificial peptide having 8-200 amino acid residues with the hydrophilic amino acids and hydrophopbic amino acids alternately bonded, which self-assembles into a beta-structure at physiological pH. Self-assembling peptides with alternating hydrophobic and hydrophilic residues or stretches which interact with the extracellular matrix are also disclosed in WO 2008/113030 A2. WO 2010/103887 A1 discloses self-assembling peptides, which comprise basic, hydrophobic and acidic amino acids of a specific primary sequence and peptide gels thereof which have high strength.

Another application, WO 2007/000979 A1, describes self-assembling peptides with polar and non-polar amino acids. The peptides are capable of forming a beta-sheet structure in which the non-polar amino acid residues are arranged on one side of the structure in the assembled form. Amphiphilic self-assembling peptides for use as stable macroscopic membranes, which are used in biomaterial applications, such as slow-diffusion drug delivery, are described in U.S. Pat. No. 6,548,630.

EP 2 327 428 A2 refers to a pharmaceutical composition comprising self-assembling peptide nanofibers, which are complementary to each other, and at least one cell for repairing damaged tissue, such as tissue after a myocardial infarction.

The use of self-assembling peptides for the delivery of bioactive agents has been described, for example in U.S. 2008/199431 A1 and in WO 2009/026729 A1. WO 2006/073889 A2 relates to a composition in which human PDGF is bound directly to peptides which assemble into a gel that slowly releases PDGF *in vivo*. WO 2006/047315 A2 proposes the attachment of therapeutic agents to self-assembling peptides using biotin/streptavidin linkages.

Kirkham et al. and Kind et al. relate to self-assembling peptide scaffolds promoting enamel remineralisation (Kirkham et al. 2007, Dent. Res. 86(5), 426-430; Kind et al. 2017, Journal of Dental Research 1-8, doi10.1177/0022034517698419).

To effectively lead to remineralisation, e.g., to treat tooth lesions, in particular, sub-surface lesions (i.e., an early caries lesion or white spot), the self-assembling peptide needs to be in a monomeric form outside the tooth lesion to enable diffusion into the lesion, and it needs to switch into an assembled form once inside the tooth lesion. If the peptide assembles outside the lesion, it cannot facilitate remineralisation within the lesion, having a low pH and high ionic strength, as the formed three-dimensional structures are too large to diffuse through the pores. Therefore, to this end, assembly of the peptide should be prevented until it reaches its site of action.

For example, WO 2014/027012 A1 and EP 2 698 162 A1 provide lyophilized solutions comprising monomeric self-assembling peptides for targeted treatment of tooth lesions. Since the solution comprising the monomeric peptides has to be applied directly onto the surface of the early caries lesion, the application is restricted to professional users, e.g. dentists. Further, pre-conditioning of the tooth to be treated is very complex, including professional cleaning of the tooth in order to remove plaque, food debris and stains as well as treatment with sodium hypochlorite and phosphoric acid, subsequent rinsing with water and drying the tooth surface. Brunton et al., 2013, Br. Dent. J. 215(4): E6, doi:10.1038/sj.bdj.2013.741) confirms that, before treatment, the lesion was cleaned with a prophylaxis paste, treated with etch solution for 20 seconds to open up the pores of the subsurface lesion and subsequently washed and dried. Lyophilised self-assembling peptide in monomeric form was rehydrated with sterile water and a single drop of the resulting solution immediately applied directly to the lesion surface. Moisture control was ensured until the P11-4 solution was no longer visible (approximately two minutes). The subjects were asked not to brush their teeth in the treated quadrant until 4 days after treatment. Schlee et al., 2014, Stomatologie 111:175-181 confirms the need for pre-treatment and moisture control.

Due to the complicated treatment, there is a substantial cost for the patient and/or the health system involved. Furthermore, there are subjects which, for psychological reasons, avoid or delay visits to the dental practitioner until caries lesions have so widely progressed that the dentist may prefer drilling and filling over the treatment approach using self-assembling peptides.

WO 2017/202940 A1 or WO 2017/202943 A1 provide personal dental care products that can be employed by the subject without the need for diagnosis of caries or intervention or a dental professional for use in treating or preventing a tooth lesion and/or in remineralizing a tooth surface comprising the self-assembling peptides in monomeric form, wherein it is emphasized that it is essential that the monomeric form is maintained after application to the subject's mouth for as long as possible.

Self-assembling peptides in assembled form (also designated polymeric self-assembling peptides) may also be applied to tooth surfaces. It has been shown in pH cycling models that the self-assembling peptide P11-4 (Curodont Protect, Credentis, Switzerland) lead to an increased mineralisation (Soares et al., 2017. Journal of Clinical and Diagnostic Research 11(4): ZC136-ZC141). A self-assembling peptide matrix was further found to prevent artificial caries lesions and lead to remineralisation of enamel around orthodontic brackets (Jablonsky-Momeni et al., 2019. Randomised in situ clinical trial investigating self-assembling peptide matrix P11-4 in the prevention of artificial caries lesions. Scientific Reports 9:269). A gel comprising the assembled self-assembling peptide (Curodont D'Senz, credentis AG, Windisch, CH) also efficiently blocked dentine tubules and may thus be used for treatment of dentine hypersensitivity (Schlee et al., Journal of Periodontology 89(6):653-660).

EP 2 853 256 A1 and WO 2015/044268 A1 teach that self-assembling peptide hydrogels, i.e., dental care products comprising assembled (polymeric) self-assembling peptides, and further comprising mineral particles of specific sizes as well as fluorophores, which may be amino acids of the self-assembling peptide, are useful for tooth whitening, wherein the self-assembling peptides and the mineral particles have a synergistic effect.

In light of the state of the art, the inventors solved the problem of providing a dental care product for use in treatment of tooth demineralisation, or for use in reducing or preventing further demineralisation of teeth in a subject with demineralised teeth. Advantageously, the dental care product of the invention is easy to administer, preferably for over the counter sale or retail, and can be applied by the patient or consumer in order to preventing demineralisation of teeth.

This problem is solved by the present invention, in particular, by the claimed subject-matter.

In a first aspect, the present invention provides a dental care product suitable for preventing further demineralisation of teeth of a subject having demineralised teeth, comprising (i) self-assembling peptides, preferably, comprising the sequence of SEQ ID NO: 3, that are capable of undergoing self-assembly at a pH below 7.5, wherein the self-assembling peptides are essentially present in the dental care product in assembled form (i.e., at least 80%, preferably at least 90%, more preferably, at least 95% or, most preferably, at least 99%), and (ii) a pharmaceutically acceptable basis, wherein the dental care product is an essentially solid product selected from the group consisting of chewing gum, soft chew, toffee, gelatin gum, chewy candy, chew toy, marshmallow, lozenge, or tablet, and wherein the dental care product is not abrasive.

The inventors have found that administration, preferably, by mastication of the dental care product of the invention leads to formation of a protective layer or film on the teeth of the subject to which it is administered. Said protective layer may then prevent further demineralisation and protects from acid attacks of the teeth. This is of particular relevance under conditions where remineralization of the teeth is reduced, and thus, remineralisation strategies, such as administration of monomeric self-assembling peptides, are less efficient than under normal conditions (e.g., in a healthy subject), or not feasible at all.

Preferably, the dental care product is a chewy product, i.e., a product which is suitable for mastication or chewing. In particular, preferably, if the dental care product is a lozenge or tablet, it is a chewable lozenge (e.g., according to Umashankar et al, 2016. International Research Journal of Pharmacy. 7. 9-16.) or a chew tablet (e.g., on the basis of compositions disclosed in Dewsbury et al. BMC Vet Res. 2019;15(1):394; Fasoulas et al, 2019. Heliyon 5(7):e02064.; Jagdale et al, 2010. Int. J. Res. Pharm. Sci. 1(3), 282-289, 2010). It may be, e.g., a soft product. The dental care product typically comprises one or more typical ingredients of the respective dental care product, e.g. typical pharmaceutically acceptable bases having a pH of less than 7.5, wherein the self-assembling peptides may be incorporated.

The self-assembling peptides in assembled form are preferably embedded in the pharmaceutically acceptable basis, preferably, e.g., embedded in a gum base. The gum base may comprise polymers (or elastomers), plasticizers and/or resins, e.g., which are typical ingredients if the product is a chewing gum.

For example, the elastomer may be any water-insoluble polymer known in the art, and includes those gum polymers utilized for chewing gum and bubblegum listed in Food and Drug Administration, CFR, Title 21, Section 172,615, as “Masticatory Substances of Natural Vegetable Origin” and “Masti catory Substances, Synthetic’.

For example, the gum base may comprise a) synthetic ingredients selected from the group consisting of butadiene-styrene rubber, isobutylene-isoprene copolymer (butyl rubber), paraffin (produced via the Fischer-Tropsch process), petroleum way, petroleum wax synthetic, polyisobutylene polyvinyl acetate, polyisobutadiene and isobutylene-isoprene copolymers, low molecular weight elastomers such as polybutene, polybuta-diene and polyisobutylene, vinyl polymeric elastomers such as polyvinyl acetate, polyethylene, vinyl copolymeric elastomers such as vinyl acetate/vinyl laurate, vinyl acetate/vinyl Stearate, ethylene/vinyl acetate, polyvinyl alcohol or mixtures thereof, and/or b) natural ingredients selected from the group consisting of
  chicle, chiquibul, crown gum, gutta hang kang, massaranduba balata, massaranduba chocolate, nispero, rosdinha, Venezuelan chicle (all derived from Sapotaceae),
  jelutong, leche saspi (sorva), pendare, perillo (all derived from Apocynaceae),
  leche de vaca, niger gutta, tuno (tuno) (all derived from Moraceae),
  chilte and natural rubber (all derived from Euphorbiaceae).

Chicle is the gum base most commonly used if a natural gum base is desired, e.g., if synthetic ingredients such as remnants of mineral oils etc are to be avoided. Natural ingredients have the advantage that they are bio-degradable, which is particularly desirable for products that are typically spit out after mastication.

Synthetic ingredients are more easily commercially accessible, and they are typically cheaper.

Chewing gums of the invention may be hard or soft chewing gums. Soft chewing gums containing self-assembling peptides may be prepared, e.g., according to Shivang A Chaudhary et al., Int J Pharm Investig. 2012 Jul-Sep; 2(3); 123-133; Abolfazl Aslani et al., Adv Biomed Res. 2013, 2:72; Zumbé et al., 2001, British Journal of Nutrition 85, Suppl. 1, S31-S45 (in particular, FIG. 8); WO2014/152952A1; WO2006/127559A2 or WO2007/143989A1. Hard chewing gums may e.g. comprise, e.g., gum base, xylitol, self-assembling peptide, e.g., P11-4 (for example, about 100 μg/chewing gum), sodium bicarbonate, tartaric acid, aroma, e.g., lemon aroma.

The chewing gum may be a pressed gum, a center-filled gum (with the assembled self-assembling peptide in the center or in the coating, preferably, in the center) or a normal gum. Preferably, the assembled self-assembling peptide is embedded in the matrix of the dental care product, i.e., for a chewing gum, in the gum base, wherein homogenous embedding has the advantage that the self-assembling peptide has continuous contact with the teeth of the person upon mastication over a long term.

Alternatively, the dental care product of the invention may comprising gelatin, albumen, lecithin, a maltitol/sorbitol matrix, pectin or starch as the pharmaceutically acceptable basis, e.g., for soft chews, gelatin gums, marshmallows or chew toys. For example, marshmallows of the invention typically comprise albumen and/or gelatin, a sweetener, water, self-assembling peptides and air. Soft chews of the invention typically comprise a maltitol/sorbitol matrix and self-assembling peptides.

Pharmaceutically acceptable bases for, e.g. a gelatin-gum of the invention, may comprise, e.g., gelatin and/or pectin, water, a sugar or a sugar substitute, e.g., in the form of a syrup, tartaric acid and/or citric acid. Gelatin-gums of the invention comprise assembled self-assembling peptides, wherein typically, the self-assembling peptide is added as an assembled pre-mix. Gelatin-gums of the invention may also be coated with self-assembling peptides. Exemplary sugar-free gelatin gums and their preparation are taught in Zumbé et al., 2001, British Journal of Nutrition 85, Suppl. 1, S31-S45, in particular, in Table 13 or Table 14, wherein self-assembling peptides are added in polymeric state, or the self-assembling peptides are added in any form, e.g., partially or completely monomeric, and, as the pH in the mixture with the basis is below 7,5, this leads to self-assembly. If the dental care product comprises gelatin, it may be A or B type gelatin. The pH is not lowered to a degree that prevents gelation of the gelatin.

The subject may be a human subject, but it may also be an animal subject, e.g., pet, such as a dog, horse or cat. Chew toys (or chewy animal biscuits) may be particularly suitable forms of the dental care product suitable for animal use, e.g., for pets such as for cats, dogs or horses, in particular, dogs. Chew toys may be coated with the assembled self-assembling peptides, and/or, preferably, they incorporate them. Such embodiments provide access to treatment and prevention means for tooth demineralisation for animals at low cost and effort. Chew toys of the invention may comprise gelatin or pectin, and self-assembling peptides, typically together with a flavor enjoyed by the animal.

Toffees comprise an emulsion of fat in an aqueous system. A self-assembling peptide toffee of the invention typically comprises, in addition to the self-assembling peptide, a sugar or sugar substitute, e.g. maltitol, sorbitol, xylitol, lactitol and/or isomalt, optionally, at least partially in the form of a syrup such as maltitol syrup, a plant oil, e.g. coconut oil, soybean oil, sunflower oil, rapeseed oil, olive oil, and/or peanut oil, a gelling agent such as gelatin and/or pectin, and, optionally, vitamins, antioxidants, e.g. citric acid and/or ascorbic acid, flavors, colorants, sweeteners, e.g. acesulfame K, aspartame and/or sucralose. Exemplary sugar-free toffees and their preparation are taught in Zumbé et al., 2001, British Journal of Nutrition 85, Suppl. 1, S31-S45, in particular, in Table 12, wherein self-assembling peptides are added and the pH adapted to ensure their assembled state, or the self-assembling peptides are added in assembled state.

A peptide chewable lozenge or chew tablet of the invention may further comprise, in addition to the self-assembling peptide in assembled state, a sugar or sugar substitute, e.g. maltitol, sorbitol, xylitol, lactitol and/or isomalt, and optionally, ingredients such as an anti-oxidant, e.g. citric acid and/or ascorbic acid, flavor, colorants and sweeteners, e.g. aspartame, acesulfame K and sucralose.

The peptide concentration in the dental care product of the invention may be between 0.1 to 5000 mg peptide/kg bulk product, e.g., 0.1-1000 mg peptide/kg bulk product, 0.1-500 mg peptide/kg bulk product, preferably 0.1 to 100 mg peptide/kg bulk product, 0.5-50 mg peptide/kg bulk product, 1-20 mg peptide/kg bulk product, or most preferably, 5-15 mg peptide/kg bulk product or 8-10 mg peptide/kg bulk product. The examples below show that such concentrations allow for reduction or prevention of tooth demineralisation.

Self-assembling peptides that are preferred peptides of the invention are provided, e.g., in WO 2004/007532 A1, which is fully incorporated herein by reference. WO2004/007532A1 discloses peptides that are capable of forming three-dimensional scaffolds, thereby promoting nucleation of de-novo calcium phosphate. These artificial peptides assemble in one dimension to form beta-sheet, and higher order assemblies such as tape-like assemblies. Three-dimensional supramolecular structures of self-assembling proteins can be formed, which have an affinity for/to calcium phosphate.

Several other self-assembling peptides (SAP) which may be employed have been described in the prior art. For example, WO2010/041636A1 describes a bioadsorbable peptide tissue occluding agent containing an artificial peptide having 8-200 amino acid residues with the hydrophilic amino acids and hydrophobic amino acids alternately bonded, which self-assembles into a beta-structure at physiological pH. Self-assembling peptides with alternating hydrophobic and hydrophilic residues or stretches which interact with the extracellular matrix are also disclosed in WO 2008/113030 A2. WO2010/103887 A1 discloses self-assembling peptides, which comprise basic, hydrophobic and acidic amino acids of a specific primary sequence and peptide gels thereof which have high strength. WO2010/019651 A1 relates to other self-assembling peptides.

Another application, WO 2007/000979 A1, describes self-assembling peptides with polar and non-polar amino acids. The peptides are capable of forming a beta-sheet structure in which the non-polar amino acid residues are arranged on one side of the structure in the assembled form. Amphiphilic self-assembling peptides for use as stable macroscopic membranes, which are used in biomaterial applications, such as slow-diffusion drug delivery, are described in U.S. Pat. No. 6,548,630.

EP 2 327 428 A2 refers to a pharmaceutical composition comprising self-assembling peptide nanofibers, which are complementary to each other, and at least one cell for repairing damaged tissue, such as tissue after a myocardial infarction.

In the context of the present invention, self-assembling peptides taught in WO 2004/007532 A1 are specifically preferred. Most preferably, said self-assembling peptide is the self-assembling peptide designated oligopeptide 104 or P11-4 (SEQ ID NO: 1, QQRFEWEFEQQ) or the self-assembling peptide having SEQ ID NO: 3, QQRFOWOFEQQ (also designated P11-8), or the self-assembling peptide having SEQ ID NO: 20, QQRQEQEQEQQ (also designated P11-20), or it comprises any of said peptides. A self-assembling peptide comprising SEQ ID NO: 1 or consisting of the same is most preferred throughout the invention. It may also be a self-assembling peptide having at least 60% sequence identity to a peptide consisting of SEQ ID NO: 1, 2, 3, 4, 5, 6, 7, 8, 9, 10, 11, 12, 13, 14, 15, 16, 17, 18, 19 or 20. Preferably, the peptide has at least 70%, at least 80%, or at least 90% sequence identity to a peptide consisting of SEQ IDs, preferably, SEQ ID NO: 1, SEQ ID NO: 3 or SEQ ID NO: 20. Most preferably, the peptide has at least 60%, at least 70%, at least 80%, or at least 90% sequence identity to a peptide consisting of SEQ ID NO: 1 or is said peptide. Alternatively, the peptide may have at least 60%, at least 70%, at least 80%, or at least 90% sequence identity to a peptide consisting of SEQ ID NO: 3 or be said peptide. Alternatively, the peptide may have at least 60%, at least 70%, at least 80%, or at least 90% sequence identity to a peptide consisting of SEQ ID NO: 20 or be said peptide. Examples of self-assembling peptides that may be employed in the invention are provided in Table 1 below.

Self-assembling peptides may be modified peptides, comprising an Ac—N-terminus and/or NH2-C-Terminus, or non-modified peptides.

TABLE 1

| SEQ ID NO | sequence |
|---|---|
| SEQ ID NO: 1 (P11-4) | QQRFEWEFEQQ |
| SEQ ID NO: 2 | QQOFOWOFQQQ |
| SEQ ID NO: 3 (P11-8) | QQRFOWOFEQQ |
| SEQ ID NO: 4 | QQRFQWQFEQQ |
| SEQ ID NO: 5 | QQEFEWEFEQQ |
| SEQ ID NO: 6 | QQOFOWOFOQ |
| SEQ ID NO: 7 | EQEFEWEFEQE |
| SEQ ID NO: 8 | QQEFEWEFEQQ |
| SEQ ID NO: 9 | ESEFEWEFESE |
| SEQ ID NO: 10 | QQOFOWOFOQQ |
| SEQ ID NO: 11 | OQOFOWOFOQO |
| SEQ ID NO: 12 | SSOFOWOFOSS |
| SEQ ID NO: 13 | SSREEWEFESS |
| SEQ ID NO: 14 | SSREOWOFESS |
| SEQ ID NO: 15 | QQOFOWOFOQQ |
| SEQ ID NO: 16 | NNRFEWEFENN |
| SEQ ID NO: 17 | NNRFOWOFENN |
| SEQ ID NO: 18 | TTRFEWEFETT |
| SEQ ID NO: 19 | TTRFOWOFETT |
| SEQ ID NO: 20 (P11-20) | QQRQEQEQEQQ |

To be able to bind the mineral particles on a tooth surface, the matrix has to be able to bind the mineral particles and adhere to the tooth surface. The matrix thus comprises binding sites for the mineral particles which enable it to bind the particles, which preferably comprise calcium, on the tooth surface. For example, charged amino acid residues such as Glu or Orn on the surface of self-assembling peptides bind to hydroxyapatite particles and to the tooth surface, which is also substantially formed of hydroxyapatite. Without intending to be bound by the theory, it is believed that both reactions increase the stability of the formed complex to generate a more permanent whitening effect. A capability for three-dimensional self-organization, which is e.g., found in collagen, supramolecular assemblies or in self-assembling peptides, is important for binding. In general, highly charged surfaces will promote adhesion of the mineral particles. The protein-matrices work particularly well when their surface shows glutamate or ornithine residues which may attach to calcium phosphate or to other mineral particles. Preferably, the protein comprises 5% or more, 10% or more, 20% or more or 30% or more charged amino acid residues, such as glutamate and/or ornithine residues.

The preferred self-assembling peptides of the invention have common features that can be summarized in a consensus sequence. In particular, the self-assembling peptides used in the products of the invention comprise the sequence of the formula X1-X2-X1-X2-X1, wherein X1 is an amino acid with an acidic side chain or basic side chain, and X2 is an amino acid with a hydrophobic or polar side chain selected from the group consisting of alanine, valine, isoleucine, leucine, methionine, phenylalanine, tyrosine, tryptophan and glutamine (SEQ ID NO: 21). X2 may be an amino acid with a neutral side chain.

In a first embodiment, X1 is an amino acid with a basic side chain. If X1 is an amino acid with a basic side chain, said amino acid preferably is ornithine or arginine. Of course, in different positions in the same self-assembling peptide, X1 may be a different basic amino acid. Preferably, X1 in position 1 of SEQ ID NO: 21 is Arg, and X1 in positions 3 and 5 of SEQ ID NO: 21 are Orn. Amino acid side chains with a basic side chain will be protonated at pH values below their nominal pK values. Self-assembling peptides wherein X1 is an amino acid with a basic side chain assemble at a high pH, e.g., at a pH of more than 7.5. P11-8, the peptide of SEQ ID NO: 3 is a preferred example of such a self-assembling peptide.

In a second embodiment, preferred herein, X1 is an amino acid with an acid side chain, i.e., a side chain that includes a —COOH group. The self-assembling peptides used in these products of the invention comprise the sequence of the formula X1-X2-X1-X2-X1, wherein X1 is an amino acid with an acidic side chain, and X2 is an amino acid with a hydrophobic or polar side chain selected from the group consisting of alanine, valine, isoleucine, leucine, methionine, phenylalanine, tyrosine, tryptophan and glutamine (SEQ ID NO: 22). X2 may be an amino acid with a neutral side chain.

Amino acid side chains with a —COOH will be deprotonated at pH values above their nominal pK values. For example, amino acids which comprise a —COOH group in their side chain such as aspartic acid (Asp, D) and glutamic acid (Glu, E) are essentially deprotonated at a pH above neutral, i.e. at pH 7, because they exhibit a low pKa (Asp: 3.71; Glu: 4.15). In the self-assembling peptides used in the products of the present invention, the amino acid side chains containing a —COOH group are specifically located in the peptide chain so as to control the electrostatic interactions between neighboring peptides, i.e. so that adjacent, identical, self-assembling peptides are repelled through electrostatic interactions when the —COOH group is deprotonated to —COO—, and to dominate the association free energy in bonds between peptides. Reducing the pH below a certain threshold, i.e. the pH at which the peptide starts to undergo self-assembly, such as about pH 7.5 for P11-4 (SEQ ID NO:1), leads to protonation of some of the —COOH groups in the self-assembling peptides of the present invention which reduces the repelling electrostatic interactions between the peptides and allows self-assembly of the peptides.

Preferred examples of self-assembling peptide of the invention that are capable of undergoing self-assembly at a pH below 7.5 (in particular, having SEQID NO: 22) are P11-4 (SEQ ID NO: 1) and P11-20 (SEQ ID NO: 20).

For example, X2 may be an amino acid with a polar neutral side chain, e.g., glutamine. The self-assembling peptides used in the products of the invention may thus comprise the sequence Glu-Gln-Glu-Gln-Glu, (SEQ ID NO: 26) In this case, a preferred self-assembling peptide is P11-20.

The peptides used in the products of the invention may also comprise the sequence of the formula X1-X2-X1-X2-X1, wherein X1 is an amino acid with an acidic side chain, and X2 is an amino acid with a hydrophobic side chain selected from the group consisting of alanine, valine, isoleucine, leucine, methionine, phenylalanine, tyrosine, and tryptophan (SEQ ID NO: 23).

In a preferred embodiment, the self-assembling peptides used in the products of the invention comprise the sequence Glu-X2-Glu-X2-Glu, wherein X2 is an amino acid with a hydrophobic side chain selected from the group consisting of alanine, valine, isoleucine, leucine, methionine, phenylalanine, tyrosine, and tryptophan (SEQ ID NO: 24) or Asp-X2-Asp-X2-Asp, wherein X2 is an amino acid with a hydrophobic side chain selected from the group consisting of alanine, valine, isoleucine, leucine, methionine, phenylalanine, tyrosine, and tryptophan (SEQ ID NO: 25).

Complementary self-assembling peptides may also be used in the context of the invention. Examples for complementary peptides are provided, e.g. in EP 2 327 428 A2.

Preferably, the self-assembling peptides used in the products of the present invention comprise or consist of the sequence Gln-Gln-Arg-Phe-Glu-Trp-Glu-Phe-Glu-Gln-Gln (P11-4, SEQ ID NO: 1), or a sequence having at least 80%, preferably 90% sequence identity thereto. It is further preferred that the peptides are modified P11-4, in particular, acylated at position 1 and amidated at position 11, or a sequence having at least 80%, preferably 90% sequence identity thereto. SEQ ID NO: 1 is a preferred variant of SEQ ID NO: 23 and SEQ ID NO: 24.

For the peptides referred to herein as P11-4, the switch from the monomeric to the assembled, multimeric form is controlled by the pH. If the pH is below pH 7.5, the peptide assembles. If the pH is higher, the state of the peptide is monomeric.

The peptide having at least 80% or more sequence identity to SEQ ID NO: 1 preferably comprises glutamic acid, or aspartic acid at positions which correspond to amino acids 5, 7 and 9 of SEQ ID NO: 1. Specifically, the peptide sequence having at least 80% or more sequence identity to SEQ ID NO: 1 preferably comprises glutamic acid at positions which correspond to amino acids 5, 7 and 9 of SEQ ID NO: 1. Preferably, the remaining amino acid positions are amino acids with a hydrophobic side chain selected from the group consisting of alanine, valine, isoleucine, leucine, methionine, phenylalanine, tyrosine, and tryptophan. Preferably, the remaining amino acid positions are not amino acids that have basic side chains, i.e. amino acids that would be positively charged at a pH around neutral.

In one embodiment, the peptides used in the products of the invention comprise or consist of sequences that differ from those depicted in SEQ ID NOs: 1, 3 or 20, preferably, 1, by the replacement of 1, 2 or 3 amino acids. Generally, each of the amino acid residues within the peptide sequence of SEQ ID NOs: 1, 3 or 20 may be substituted by another residue, as long as the resulting peptide is still capable of undergoing self-assembly at a pH value below 7.5. It is preferred that the substitutions are conservative substitutions, i.e. substitutions of one or more amino acid residues by an amino acid of a similar polarity, which acts as a functional equivalent. Preferably, the amino acid residue used as a substitute is selected from the same group of amino acids as the amino acid residue to be substituted. For example, a hydrophobic residue can be substituted with another hydrophobic residue, or a polar residue can be substituted with another polar residue having the same charge. Functionally homologous amino acids which may be used for a conservative substitution comprise, for example, non-polar amino acids such as glycine, valine, alanine, isoleucine, leucine, methionine, proline, phenylalanine, and tryptophan. Examples of uncharged polar amino acids comprise serine, threonine, glutamine, asparagine, tyrosine and cysteine. Examples of charged polar (basic) amino acids comprise histidine, arginine and lysine. Examples of charged polar (acidic) amino acids comprise aspartic acid and glutamic acid.

Further, the peptides used in the products of the invention may be structurally modified in one or more amino acid positions, e.g. by the introduction of one or more modified amino acids. According to the invention, these modified amino acids may be amino acids that have been changed by e.g. biotinylation, phosphorylation, glycosylation, acetylation, branching and/or cyclization. Further, the peptides of the invention may additionally or alternatively contain other modifications, such as terminal blocking groups, formyl-, gamma-carboxyglutamic acid hydroxyl-, methyl-, phosphoryl-, pyrrolidone carboxylic acid-, and/or sulphate-groups. In a preferred embodiment, all peptides of the invention are acetylated at their N-terminus and/or amidated, e.g. with an $NH_2$-group, at their C-terminal end, most preferably, both. A particularly preferred embodiment is a peptide P11-4 that is N-terminally acetylated and C-terminally amidated with a $NH_2$-group.

The size of the self-assembling peptides used in the products of the invention is not specifically limited. The peptides of the invention may be of any length that allows self-assembly in a pH-dependent manner. Preferably, the peptides will have a size of about 5-200 amino acids, more preferably, 9-100 amino acids, 10-50 amino acids, 10-30 amino acids or 11-20 amino acids. Even more preferably, the self-assembling peptides will have a length of about 27 amino acids, 24 amino acids, 21 amino acids, 15 amino acids, or 11 amino acids. In a particularly preferred embodiment, the self-assembling peptides have a length of 11 amino acids.

The self-assembling peptides may be prepared by any suitable method that is commonly known in the field of peptide synthesis. For example, peptides with a length of more than 50 amino acids may be prepared by recombinant methods. In one embodiment, the self-assembling peptides are produced as fusion peptides. As used herein, a fusion peptide refers to a fusion of a first amino acid sequence comprising the self-assembling peptide of interest which is N-terminally or C-terminally linked to a second amino acid sequence. The second amino acid sequence may be an affinity tag, i.e. an amino acid sequence that is fused to the N-terminus or C-terminus of the self-assembling peptide and which exhibits an increased affinity to another compound, thereby allowing purification of the fusion peptide. Preferably, the tag sequence is removed from the self-assembling peptide of interest after purification, for example by providing a proteolytic cleavage site between the self-assembling peptide and the affinity tag. In one embodiment, the self-assembling peptide is prepared as disclosed in Kyle et al., 2010, Biomaterials 31, 9395-9405 and Kyle et al. 2009, Trends in Biotechnol. 27 (7), 423-433.

Smaller self-assembling peptides are usually prepared by chemical synthesis. For example, the peptides may be chemically synthesized by solid phase or liquid phase methods. Protocols for solution-phase chemical synthesis of peptides have been described (see, for example, Andersson et al., Biopolymers 55:227-250, 2000). For solid phase synthesis the technique described by Merrifield (J. Am. Chem. Soc., 1964, 85, 2149-2154) may be used. In this approach, the growing peptide is anchored on an insoluble resin, and unreacted soluble reagents are removed by filtration or washing steps without manipulative losses. Solid phase peptide synthesis can be readily performed by use of automated devices.

The peptides used in the products of the invention may comprise any natural, proteinogenic amino acid. In addition, the peptides may also comprise unusual, non-proteinogenic amino acids, such as carnitine, gamma-aminobutyric acid (GABA), hydroxyproline, selenomethionine, hypusine, lanthionine, 2-aminoiso-butyric acid, dehydroalanine, ornithine (Orn, O), citrulline, beta alanine (3-aminopropanoic acid), and the like. Non-proteinogenic amino acids can be incorporated into the peptide by post-translational modification or by direct incorporation during chemical synthesis of the peptide.

Self-assembling peptides used in the products of the invention undergo self-assembly in response to a certain pH and ionic strength. In one embodiment, preferred self-assembling peptides for use according to the invention are selected such that they undergo self-assembly as soon as the pH of their environment drops below a certain pH, e.g. below pH 7.5. The pH at which the self-assembling peptides of the invention start to undergo self-assembly is below 7.5, preferably below 7.2, more preferably below 7.0. For example, the pH at which the self-assembling peptides P11-4 (SEQ ID NO:1) and terminally modified P11-4 start to undergo self-assembly is about 7.5. This means that the self-assembling peptides start to self-assemble to a significant extent when the pH drops below 7.5.

As used herein, the pH at which the self-assembling peptide starts to undergo self-assembly refers to the pH below which a significant extent of self-assembly of the peptides in solution is observed, which means that at least about 25%, about 30%, about 35%, about 40%, about 45%, about 50%, about 55%, about 60%, about 65%, about 70%, about 75%, about 80%, about 85%, about 90%, about 95%, about 99% or even about 100% of the peptides found in the dental care product are assembled. In a preferred embodiment, at least about 25% of the peptides found in the dental care product are assembled below the pH at which the peptide starts to undergo self-assembly.

Preferably, at the pH which initiates self-assembly, e.g. about pH 7.5 for P11-4 and modified P11-4, only about 20% or less, preferably only about 15% or less, more preferably 10% or less, and even more preferably 5% or less of the peptides are in a multimeric state.

In contrast, below the pH which initiates self-assembly, e.g. below pH 7.5 for P11-4 (SEQ ID NO:1), a significant extent of self-assembly of the peptides in solution is observed, which means that at least about 25%, about 30%, about 35%, about 40%, about 45%, about 50%, about 55%, about 60%, about 65%, about 70%, about 75%, about 80%, about 85%, about 90%, about 95%, about 99% or even about 100% of the peptides found in the solution are assembled, i.e. multimeric or polymeric.

Preferably, the ionic strength at which the peptides undergo self-assembly is physiologic ionic strength.

As used herein, "self-assembly" of the peptides refers to the spontaneous and reversible organization of peptides with other peptides of their own kind (or peptides having a similar structure) into multimeric assemblies by non-covalent interactions. Non-covalent interactions that are responsible for forming the multimeric assemblies include van-der-Waals, pi-stacking, hydrogen bonds, polar and ionic interactions between the amino acid backbones and/or the amino acid side chains of the peptides.

The self-assembling peptides used in the products of the invention are preferably assembled into beta-pleated sheets. In the beta-pleated sheet, the sheet-like structure is created by a series of hydrogen bonds between residues in different polypeptide chains or between residues in different sections of a folded poly-peptide. Typically, adjacent polypeptide chains in beta-pleated sheets are anti-parallel, which means that they run in opposite directions. However, the adjacent chains may also run parallel. If several polypeptide chains participate in the sheet formation, the sheet is a rigid wall-like structure. Multiple pleated sheets provide the requisite toughness and rigidity. The peptides that can be used in products of the invention form stable secondary structures upon self-assembly. Preferably, the peptides used in the invention will form long "beta-tapes" comprising a beta-pleated structure of a single molecule in thickness. The peptides may form complex structures during assembly, such as helical tapes (single-molecule thick), twisted ribbons (double tapes), fibrils (twisted stacks of ribbons) and fibers (entwined fibrils). With decreasing pH, helical tapes, twisted ribbons, fibrils and at last fibers may form. Preferably, the dental care product of the invention comprises fibers of the self-assembling peptide.

As is known to the skilled person, the assembly state of peptides is also influenced by the ionic strength. The ionic strength of a solution is a function of the concentration of all ions present in that solution. Thus, even at a pH above the pH at which the peptide starts to undergo self-assembly, i.e. when the peptide is substantially monomeric in solution, a particularly high ionic strength is able to trigger the assembly of the peptide.

At a ionic strength in the physiological range, i.e. the ionic strength corresponding to 150 mM NaCl, P11-4 is assembled at neutral pH (Carrick et al., 2007. Tetrahedron 63(31):7457-7467). The skilled person will know how to determine and measure the ionic strength of a solution. The ionic strength I is generally calculated according to the formula $I=\frac{1}{2}\Sigma z_i^2 b_i$, wherein z is the valence factor and $b_i$ is the molality [mol/kg $\{H_2O\}$] of the $i^{th}$ concentration. The summation, Σ, is taken over all ions in a solution. For example, the ionic strength of a 150 mM NaCl solution is approximately 0.15. This is also approximately the ionic strength of blood. The ionic strength of saliva present in the oral cavity is generally much lower, such as e.g. approximately 0.04.

The skilled person is aware of numerous methods to determine the ionic strength of a preparation. For example, the ionic strength may be estimated from a measurement of the electric conductance ($S=I/\Omega=A/V$) of a solution via the Russell's factor as follows: $I=1.6\times10^{-5}\times$Specific Conductance [μS/cm]. A 150 mM NaCl solution has a conductance of approximately 80-100 mS/cm. Thus, according to the above and the described estimation of the electric conductance, the dental care product will have an electric conductance of below 100 mS/cm, preferably below 80 mS/cm.

Further, the skilled person is aware of numerous methods to determine the pH at which a peptide of the present invention will start self-assembly at a given ionic strength. Suitable methods are denoted e.g. in a publication by Aggeli et al. (2003, J Am Chem Soc, 125, 9619-9628).

The skilled person will be able to determine whether essentially all of the self-assembling peptides are in a assembled form by means of routine experimentation. For example, the assembly state of the peptides in solution can be determined by nuclear magnetic resonance (NMR), such as $^1$H-NMR, by circular dichroism analysis, by dynamic light scattering (DLS) analysis, diffusing-wave spectroscopy, native electrophoretic methods, viscosity measurements (rheology), Quartz crystal microbalance with dissipation monitoring (QCMD) and the like, preferably by native electrophoretic methods. The presence of fibers of self-assembled peptide may be detected by TEM, as described in the examples below.

It is known to the skilled person that the peptide concentration may influence the assembly of peptides, i.e. a particularly high peptide concentration may trigger assembly. Further, an exceptionally low peptide concentration may prevent assembly of the peptides of the invention, i.e. even under low pH conditions as present in tooth lesions and the oral cavity.

Typically, the pH of the dental care product of the invention is in the range in which the dental care product of the invention is assembled. Accordingly, for a self-assembling peptide comprising SEQ ID NO: 22, the pH preferably is below 7.5, or, for a self-assembling peptide of SEQ ID NO: 21, wherein X1 is an amino acid with a basic side chain, the pH is above 7.5. However, it is also possible to vary the pH, e.g., to a pH of up to 8.5 or even up to 11 (Carrick et al., 2007) for a self-assembling peptide comprising SEQ ID NO: 22 such as P11-4, while maintaining the self-assembled peptide in assembled form, or to a pH of down to 5 for a self-assembling peptide of SEQ ID NO: 21, wherein X1 is an amino acid with a basic side chain. E.g., a high ionic strength and or the concentration of the self-assembling peptide may lead to maintenance of the assembled form.

Thus, for example, it is possible to prepare a dental care product of the invention having a slightly basic pH, e.g., pH 7.5-8 or 8-8.5, comprising P11-4 or P11-20 (preferably, P11-4) in assembled form. In this case, a premix of assembled peptide, preferably, comprising predominantly fibers of the self-assembled peptide, is mixed with a matrix buffered at the desired pH, wherein the ionic strength and/or concentration of self-assembling peptide are high enough to maintain the self-assembling peptide in assembled form. Upon administration, e.g., after a meal or acidic drink, the basic pH of the dental care product may neutralize the pH of the mouth. In this environment, assembled self-assembling peptide may then form a protective layer on teeth.

With regard to dental care products of the invention comprising SEQ ID NO: 21, wherein X1 is an amino acid with a basic side chain, e.g., P11-8, a slightly acidic pH, e.g., in the range of 7-7.5, 6-7 or even 5-6, wherein the assembled form is maintained, may be advantageous, because an acidic pH is typically considered more tasty by humans.

Suitable buffers and pH modulating agents for obtaining the desired pH are known in the art.

To prevent an abrasive effect on teeth that are already demineralised, the dental care products of the invention are not abrasive. Abrasion is usually caused by particles. In particular, the dental care products of the invention are free or essentially free of relevant concentrations of abrasive agents, in particular, essentially free of particles, in particular, mineral particles. The commonly used abrasive agents are calcium carbonate, silica, aluminum hydroxide and phosphates of aluminum or calcium. If the dental care products of the invention were abrasive (like typical toothpastes), that would lead to further abrasion or erosion of the already demineralized teeth as they are intended for chewing.

Abrasion depends on different parameters, in particular, the hardness, the size, and the form of particles. Preferably, the dental care product does not comprise significant amounts of hard particles, in particular, particles having a MOSH hardness higher than the MOSH hardness of dentin which is 3. Larger particles are more abrasive than small particles. Thus, the dental care product preferably does not comprise significant amounts of large particles, e.g., having a size of 1 μm or more, 0.5 μm or more or 0.1 μm or more. Round particles are less abrasive than particles with edges. Thus, the amounts of round particles that may be contained are higher than amounts of otherwise comparable particles with edges.

Preferably, the dental care products of the invention do not comprise 0.4 wt % or more of mineral particles having a size of at least 0.1 μm, more preferably, they comprise less than 0.3 wt % of mineral particles having a size of at least 0.1 μm, less than 0.2 wt % of mineral particles having a size of at least 0.1 μm or less than 0.1 wt % of mineral particles having a size of at least 0.1 μm or less than 0.01 wt % of mineral particles having a size of at least 0.1 μm. They may also be free of mineral particles).

To improve taste and acceptance of the products, dental care products of the invention may comprise sugar and/or sugar substitutes, which, preferably, do not promote tooth decay, e.g., polyols or sugar alcohols such as sorbitol, mannitol, maltitol, lactitol, isomalt, xylitol and/or erythritol, or D-tagatose and/or trehalose. Advantageously, the dental care product of any of the preceding embodiments that is free of cariogenic sugars such as sucrose. Thus, preferably, the products are sugar-free products, i.e., they do not comprise sucrose or glucose in significant amounts, or not at all. Sugar-free products based on suitable modifications of preparations disclosed e.g., by Zumbé et al., 2001, British Journal of Nutrition 85, Suppl. 1, S31-S45, further comprising the self-assembling peptides and with a pH controlled to ensure assembled state of the peptides, as disclosed herein, e.g., by choice of appropriate buffers and pH, may be used.

It is particularly advantageous if the dental care product, in addition to the self-assembling peptides, comprises a polyol such as xylitol, erythritol or sorbitol, which have been shown to be anti-cariogenic, preferably, xylitol. It also reduces biofilm and plaque and thus facilitates access of the self-assembling peptides of the invention to the tooth surface and potential lesions. Of course, xylitol is not used for application in dogs, cows, goats, rabbits or other animals for which the substance is toxic. Xylitol can be used in products of the invention for use in human subjects or e.g., cats, preferably, human subjects.

The dental care product of the invention may further comprise, e.g., aroma such as lemon aroma, caramel, vanillin, menthol, conserving agents such as ethanol, sodium benzoate, coloring agents such as solvent red, acid blue 3, active agents such as fluorides, preferably, in the form of tertiary amines, such as amine fluoride, or organic fluoride such as sodium monofluorophosphate, potassium nitrate, and/or oxalate.

As long as the dental care product of the invention is not abrasive, as defined above, it may comprises a phosphate such as sodium phosphate, calcium phosphate, e.g. hydroxyapatite. Phosphates may help towards remineralisation, and may also have cleaning effects. Phosphates may e.g., be present in solution.

The dental care product of the invention may comprises a pyrophosphate. These have a hydrophilic action on the tooth surface and may prevent extrinsic staining.

The dental care product of the invention may comprise a pH controlling agent such as sodium carbonate/bi-carbonate or urea.

Buffering agents that may be used in the context of the invention may be one or more of, e.g. an alkali metal carbonate, an alkali metal bicarbonate, an alkaline earth metal carbonate, an alkali metal citrate or an alkali metal phosphate, or any mixture thereof. Preferred buffering agents are sodium carbonate, potassium carbonate, sodium bicarbonate, potassium bicarbonate, calcium carbonate, potassium citrate or dipotassium phosphate, or any mixture thereof. More preferably, the buffering agent is sodium carbonate, sodium bicarbonate, potassium carbonate, potassium bicarbonate, potassium citrate and dipotassium phosphate, or any mixture thereof. Especially, it is sodium carbonate, sodium bicarbonate, potassium carbonate or potassium bicarbonate, or any mixture thereof (e.g., as disclosed in U.S. Pat. No. 9,511,021).

Of note, even if the pH of the dental care product is basic, i.e., has a pH above pH 7.5, e.g., pH 7.5-8, a pre-formulated assembled self-assembling peptide maintains its assembled form if the ionic strength is high enough. Thus, a slightly basic dental care product of the invention may be used after eating or drinking to neutralize an acid pH while still able to deliver assembled self-assembling peptide. However, in the context of human consumption, an acidic pH often leads to a more pleasant taste.

In another aspect, the invention provides a process for preparing a dental care product of any of embodiments 1-13, comprising steps of a) providing a first matrix of assembled self-assembling peptide,
b) providing a pharmaceutically acceptable basis as a second matrix, wherein steps a) and b) can be carried out in any order, and
c) mixing the first and the second matrices, optionally, together with other ingredients,
d) forming the dental care product and,
e) optionally, packaging the dental care product.

The first matrix of assembled self-assembling peptide of step a) may e.g., be prepared by drying a solution having a pH below 7.5. The matrix may be a gel or a dry substance, e.g., obtainable by spray drying, lyophilisation or evaporation.

Preferably, for step a), the peptide is first monomerised by raising the pH to at least 8. Then, the pH is titrated, preferably, slowly titrated to less than pH 7.5 to allow for ordered formation of beta-sheets, fibrils and fibers of the self-assembling peptide. Advantageously, the pH is lowered until essentially all self-as-sembling peptide is present in assembled (or polymeric) form.

Alternatively, after production of self-assembling peptide, the pH is controlled, and, if required, the pH is lowered to a pH of less than 7.5, leading to formation of beta-sheets, fibrils and fibers of the self-assembling peptide, if not already present. Monomerisation and then titration to a low pH (<7.5) is preferred, as the structures of self-assembling peptide are more ordered, and random coil structures are avoided. This leads to a more homogenous and more reproducible product.

The pharmaceutically acceptable basis, i.e., the second matrix, may be any of the basis described herein. Preferably, it is a gum base, as defined above. Preparation of such gum bases is known in the state of the art.

In step c), the first and the second matrix are mixed. Preferably, they are homogenised. The homogenisation leads to a substantially homogenous distribution of self-assembling peptide in the pharmaceutically acceptable basis of the dental care product. The homogenisation may be carried out by mixing, e.g., with a blender, homogenization equipment, pass through-homogenizer, disperser, or with rotating membranes etc., preferably, with blender.

In any case, it is preferred that the self-assembling peptides are already in assembled form before mixing with the pharmaceutically acceptable basis. The inventors have found that this facilitates self-assembly of the matrix of self-assembled peptides, in particular, of fibrils and fibers of self-assembling peptide. Surprisingly, homogenisation does not lead to disintegration of such matrix structures. The dental care product thus preferably comprises fibrils and/or fibers of assembled self-assembling peptide, e.g., fibrils of P11-4.

The dental care product may then be formed, e.g., by extrusion, by forming the mixture in a mold, e.g., by pouring or applying pressure, and/or by cutting, tearing, or forming a hardened mixture of the matrix of assembled self-assembling peptide and the self-assembling peptide. For example, chewing gums are typically cut into strips, but they may also be shaped into balls.

In one embodiment, a matrix of assembled self-assembled peptide, e.g., prepared as in step a, may be applied to a dental care product, e.g., a chewing gum, in particular, a chewing gum ofd the invention, in a coating step. For example, a solution comprising assembled self-assembling peptide such as P11-4, preferably, having a pH below 7.5, may be applied as a coating, optionally, by spray drying.

The dental care product may then be packaged. Packaging may be an individual packaging for each product, e.g., in a paper or foil or a combination thereof, such as customary for chewing gums, and/or a bulk product packaging, e.g.., several individual dental care products in one packaging, e.g., in a glass, a paper packaging or, a plastic back. Of course, several packages can then be further packaged e.g., for retail.

The packaged dental care product may comprise printed information relating to the medical and/or cosmetic use of the product, as disclosed herein, e.g., a leaflet or a label.

The invention also provides a dental care product of that is obtainable by a process of the invention.

In one aspect, the invention provides a dental care product of, as described herein, for use in reducing demineralisation of a tooth surface of a subject with demineralised teeth, in particular, for reducing further demineralisation of a tooth surface of a subject with demineralised teeth.

In the context of the invention, demineralized teeth does not necessarily mean the presence of caries, but rather, a shift in the balance of demineralisation and remineralisation towards demineralisation of teeth. For example, the subject may have a disease or disorder favouring demineralisation, e.g., a disease or disorder that prevents or reduces the remineralisation of teeth that occurs in healthy subjects. The inventors have surprisingly found, that, in such cases, where remineralisation often does not lead to satisfactory results, application of the dental care product of the present invention may help to prevent or reduce further demineralisation. For example, the dental care product may be for use in treating a subject having xerostomia, hyposalivation, bruxism, dentine hypersensitivity and/or tooth erosion, i.e., the subject with demineralized teeth may be a subject having one or more of these diseases or disorders. Preferably, through the administration of the dental care product of the invention, in these diseases, a layer of self-assembling peptides forms on the tooth surface which may be eroded or demineralized, i.e., which acts as a sacrificial layer before the tooth itself can be damaged.

In one embodiment, the subject has xerostomia. Xerostomia is the subjective sensation of dry mouth, which is often (but not always) associated with hypofunction of the salivary glands. Xerostomia may be associated with a change in the composition of saliva, or reduced salivary flow, or have no identifiable cause.

This symptom is very common and is often seen as a side effect of many types of medication. It is more common in older people (mostly because this group tend to take several medications), or in persons abusing drugs, e.g., chronic users of methamphetamine, or in persons who breathe through their mouths. Dehydration, radiotherapy involving the salivary glands, chemotherapy and several diseases can cause reduced salivation (hyposalivation), or a change in saliva consistency and hence a complaint of xerostomia. Sometimes there is no identifiable cause, and there may sometimes be a psychogenic reason for the complaint.

Hyposalivation is a clinical diagnosis that is made based on the history and examination but reduced salivary flow rates have been given objective definitions. Salivary gland hypofunction has been defined as any objectively demonstrable reduction in whole and/or individual gland flow rates. An unstimulated whole saliva flow rate in a normal person is 0.3-0.4 ml per minute, and below 0.1 ml per minute is significantly abnormal. A stimulated saliva flow rate less than 0.5 ml per gland in 5 minutes or less than 1 ml per gland in 10 minutes is decreased. The term subjective xerostomia is sometimes used to describe the symptom in the absence of any clinical evidence of dryness. Xerostomia may also result from a change in composition of saliva (from serous to mucous). Salivary gland dysfunction is an umbrella term for the presence of xerostomia, salivary gland hyposalivation, and hypersalivation (https://en.wikipedia.org/wiki/Xerostomia).

Thus, in one embodiment, the xerostomia is associated with hyposalivation, e.g., with an unstimulated whole saliva flow rate below 0.1 ml per minute. The subject may also have hyposalivation without a subjective feeling of dry mouth.

Reduced salivation significantly decreases the rate of remineralisation of teeth, and thus shifts the balance towards demineralisation. Without the buffering effects of saliva, tooth decay becomes a common feature and may progress much more aggressively than it would otherwise ("rampant caries"). It may affect tooth surfaces that are normally spared, e.g., cervical caries and root surface caries. This is often seen in patients who have had radiotherapy involving the major salivary glands, termed radiation-induced caries.

Reduced salivation may be due to physiologic effects, e.g., anxiety or dehydration, or due to xerogenic medication, e.g., anticholinergic, sympathomimetic, or diuretic drugs. Smoking is another possible cause. Administration of other recreational drugs such as methamphetamine, cannabis, hallucinogens, or heroin, may also lead to xerostomia, and demineralisation of teeth. Xerostomia may also be caused by autoimmune conditions which damage saliva-producing cells, such as Sjögren's syndrome, e.g., primary or secondary Sjögren's syndrome. Xerostomia may also be associated with celiac disease. Hormonal disorders, such as poorly controlled diabetes, chronic graft versus host disease or low fluid intake in people undergoing haemodialysis for renal impairment may also result in xerostomia, due to dehydration. Xerostomia may be a consequence of infection with hepatitis C virus (HCV). A rare cause of salivary gland dysfunction may be sarcoidosis. Infection with Human Immunodeficiency Virus or Acquired immunodeficiency Syndrome (AIDS) can cause a related salivary gland disease known as Diffuse Infiltrative Lymphocytosis Syndrome (DILS).

In one embodiment, the subject has bruxism, i.e., excessive teeth grinding or jaw clenching. Several symptoms are commonly associated with bruxism, including hypersensitive teeth, aching jaw muscles, headaches, tooth wear, and damage to dental restorations (e.g. crowns and fillings). In this context, the dental care product of the convention does not necessarily reduce the teeth grinding or jaw clenching, but it functions in preventing or reducing further demineralisation of teeth.

The subject may also have dentine hypersensitivity. Dentin hypersensitivity is associated with dental pain which is sharp in character and of short duration, arising from exposed dentin surfaces in response to stimuli, typically thermal, evaporative, tactile, osmotic, chemical or electrical; and which cannot be ascribed to any other dental disease. A degree of dentin sensitivity is normal, but pain is not usually experienced in everyday activities like drinking a cooled drink.

The subject may also have tooth erosion. Acid erosion is a type of tooth wear. It is defined as the irreversible loss of tooth structure due to chemical dissolution by acids not of bacterial origin. Acid erosion begins in the enamel, causing it to become thin, and can progress into dentin, giving the tooth a dull yellow appearance and leading to dentin hypersensitivity. The most common cause of erosion is by acidic foods and drinks. In general, foods and drinks with a pH below 2-3 have been known to trigger dental erosion effects. Gastroesophageal reflux disease may also be associated with erosion.

Preferably, the subject to which the dental care product is to be administered has a clinical oral dryness scale of at least 1, preferably, at least 4 or, most preferably, at least 7 on the Challacombe Scale.

The dental care product of the invention may be administered to the mouth of the subject and be subject to mastication. Advantageously, it is to be maintained in the mouth for at least 3 min. The dental care product may also be maintained in the mouth for at least 4 min, preferably, for at least 5 min or at least 10 min.

The inventors have found that this allows for an at least partial separation of the two matrices of the dental care product, namely, the matrix of assembled self-assembling peptides, which leads to formation of a protective layer of assembled self-assembling peptides on the tooth surface, and, e.g., the gum matrix of the dental care product, which e.g., contributes to cleaning of the teeth The formation of the protective layer of self-assembling peptide reduces further demineralisation. In contrast to an increased remineralisation, this effect is not dependent on the presence of saliva, and it can thus also be exploited in subjects with reduced or absent salivation.

A dental care product of the invention requiring or allowing for chewing, such as candy, lozenge, gelatin-gum, toffee, chewing gum, biscuit or chew toy, in particular, such forms associated with a long (e.g., 5 min or more) application such as chewing gum (for humans) or chew toy (for animals), are associated with particular advantages, as their use may at the same time reduce biofilm or plaque, and thus facilitate access to tooth surfaces and potential lesions. Such products also increase salivation.

Thus, preferably, upon mastication of the dental care product of the invention, the gum base cleans the tooth surface (e.g., it reduces the presence of pellicle and/or biofilm/and/or food debris and/or calculus and/or stains, preferably, all of these), and the matrix of assembled self-assembling peptide provides a film on the tooth surface that reduces or prevents demineralisation of the tooth surface.

It is advantageous if the dental care product is to be masticated, i.e., chewed, by the subject. The inventors have found that, preferably, five minutes mastication of a dental care product of the invention increase the salivary flow by a factor of at least 10.

Optionally, the dental care products further comprises a sialogogue, e.g., a parasympathomimitic drug. Thus, the dental care product may, in addition to reducing further demineralisation, also reduce other symptoms of xerostomia, in particular, the feeling of dry mouth. This is however not required in the context of the invention.

In comparison to other galenic forms of self-assembling peptide, e.g., toothpastes or gels, the dental care product of the invention may be more easily administered by the subject, e.g., it can be administered at the work-place or while travelling, and it does not necessitate the use of a wash basin or water. The ease of administration increases the compliance of the subjects. Another advantage compared to toothpastes is the absence of abrasive agents that are typically contained in toothpastes, which is especially beneficial for subjects already having pathologically demineralized teeth. Further, the essentially dry formulation of the dental care product of the invention increases the stability of the product, which can be stored for a longer time.

The dental care product of the invention may, e.g., be administered at least once a day, preferably, at least twice a day. It may also be administered at least three times a day, four times a day or five times a day. For example, it may be administered when the subject has an increased feeling of dry mouth. The dental care product may also be administered after a meal or snack, optionally, instead of brushing the teeth. The dental care product may also be administered after waking to reduce xerostomia. Preferably, the subjects apply the dental care product regularly, so that further demineralisation can be avoided by use of the product of the invention. For example, the dental care product may be administered for at least two consecutive days, for at least three consecutive days, or at least 5 consecutive days. The product preferably is administered for at least a week, at least two weeks, at least three weeks, at least four weeks, at least a month, at least 2 months, at least 6 months, or for at least a year. The product can be administered for the rest of the lifetime, e.g., daily.

Advantageously, the dental care product reduces the incidence, and preferably, prevents caries, in particular, in subjects with demineralised teeth. The dental care product of the invention may also reduce pain associated with dentine hypersensitivity.

As used herein, "subject" refers to any subject having teeth, e.g., a mammal such as a human, a dog, a feline such as a cat, a rodent such as a mouse, rat, hamster, guinea pig, a cow, a horse, a camel, a sheep, a goat or another pet, farm or zoo animal having teeth. Preferably, the subject is a human.

In the context of the invention, unless explicitly mentioned or clear from the context, "a" is not limited to the singular, but can also mean "one or more". For example, reference to "a tooth", unless explicitly mentioned otherwise, includes reference to more than one tooth, in particular, all teeth of the subject.

The following examples and embodiments are intended to illustrate, but not to limit the invention. All references cited herein are herewith fully incorporated.

BRIEF DESCRIPTION OF THE FIGURES

FIG. 3: Examples of a chewing gums of the invention.

EXAMPLES

Figure 1:
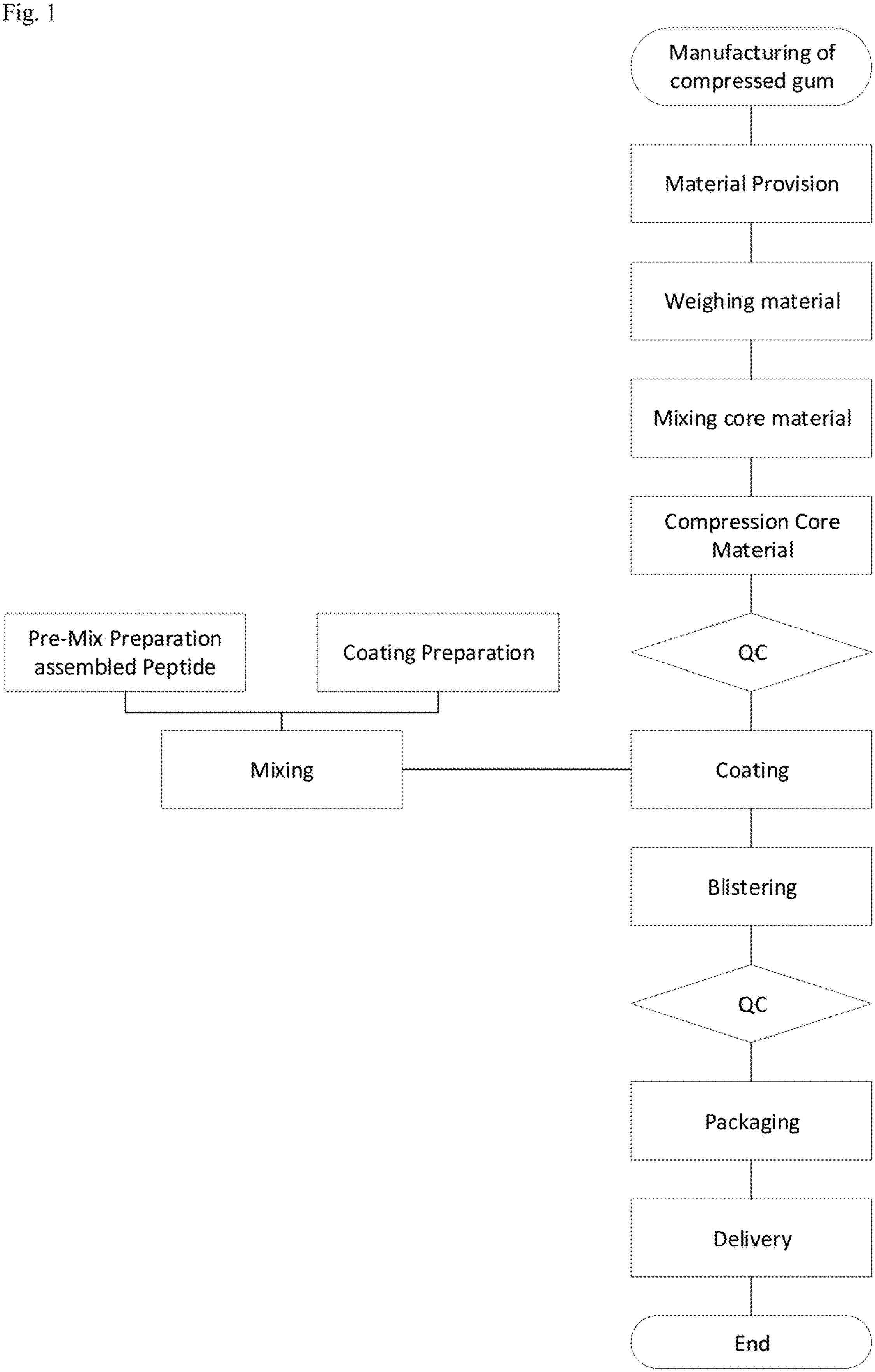
FIG. 1: Generic Manufacturing Flow for the preparation of coated chewing gums
Figure 2:
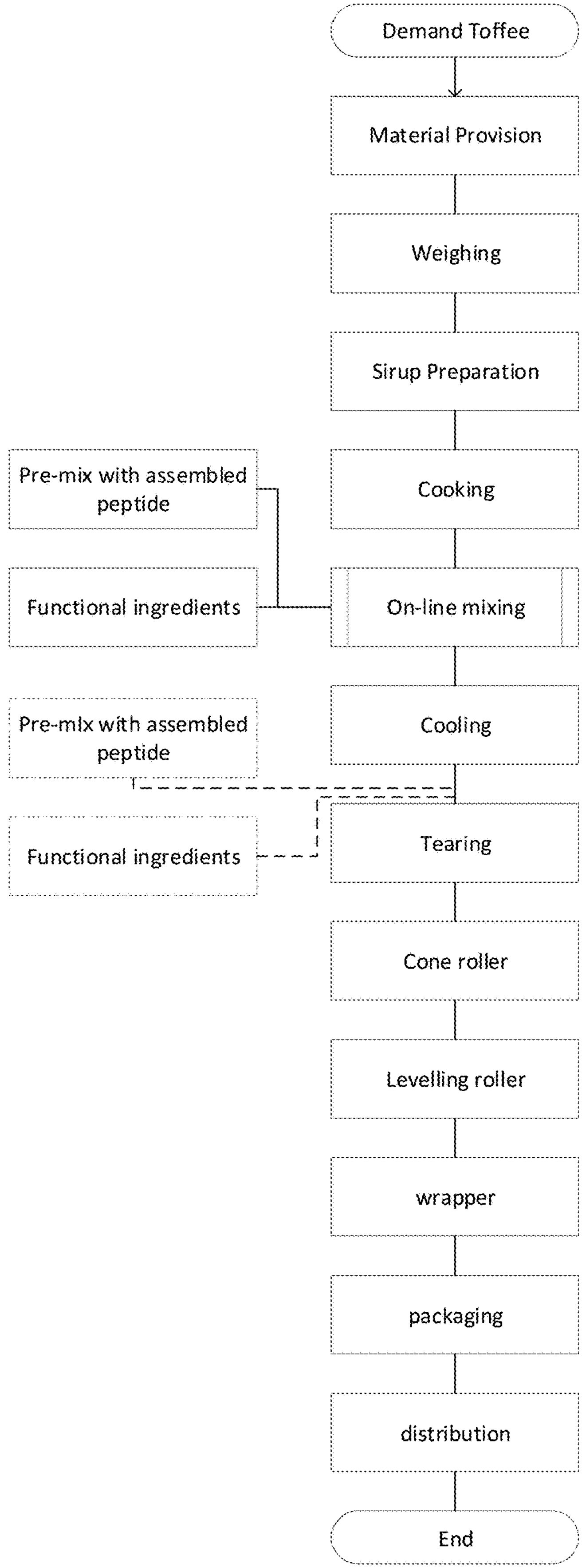
FIG. 2: Generic manufacturing flow for the production of toffees. The addition of temperature sensitive material may be after the online mixer.
Figure 3A:
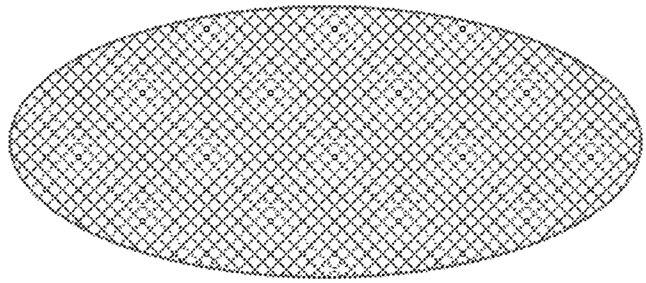
FIG. 3A: Chewing gum product comprising assembled self-assembling peptide and the gum base, e.g., chicle.
Figure 3B:
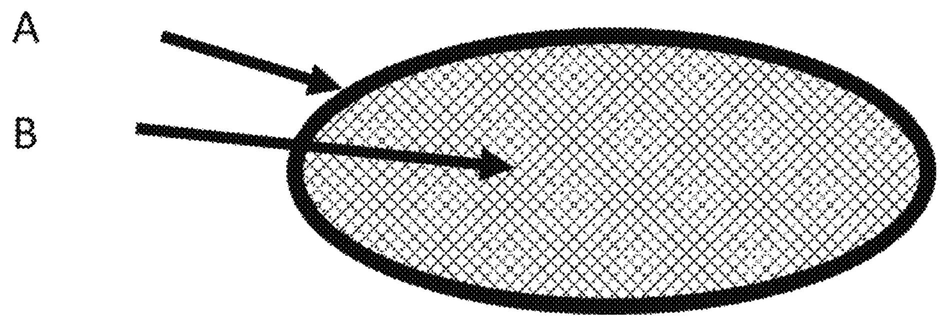
FIG. 3B: Chewing gum A) Shell comprising taste B) matrix comprising assembled self-assembling peptide and the gum base, e.g., chicle.
Figure 3C:
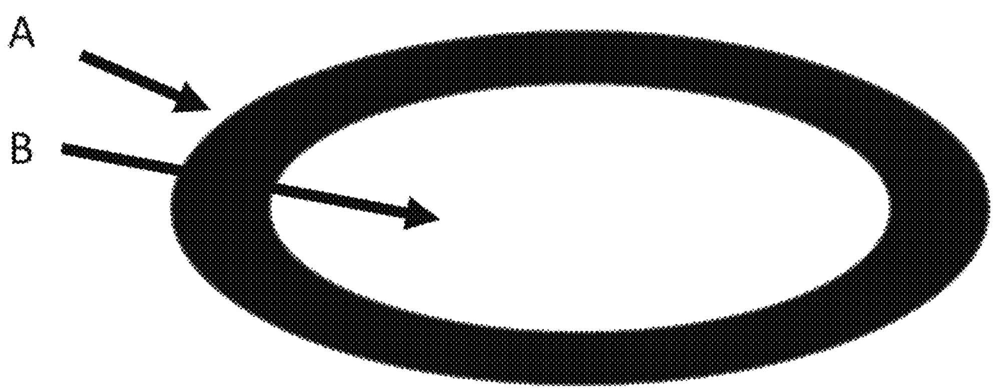
FIG. 3C: Coated chewing gum: A) shell/coating comprising the taste and/or self-assembling peptide. B) core comprising the assembled self-assembling peptide and gum base matrix.
Figure 3D:
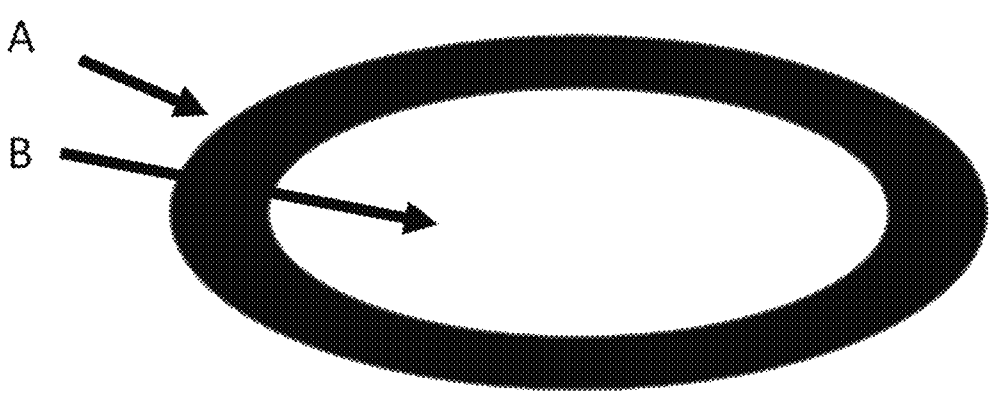
FIG. 3D: Coated chewing gum: A) shell comprising the assembled self-assembling peptide. B) core comprising the gum base, e.g., chicle. Gum base may be made from compressed gum.
Figure 4:
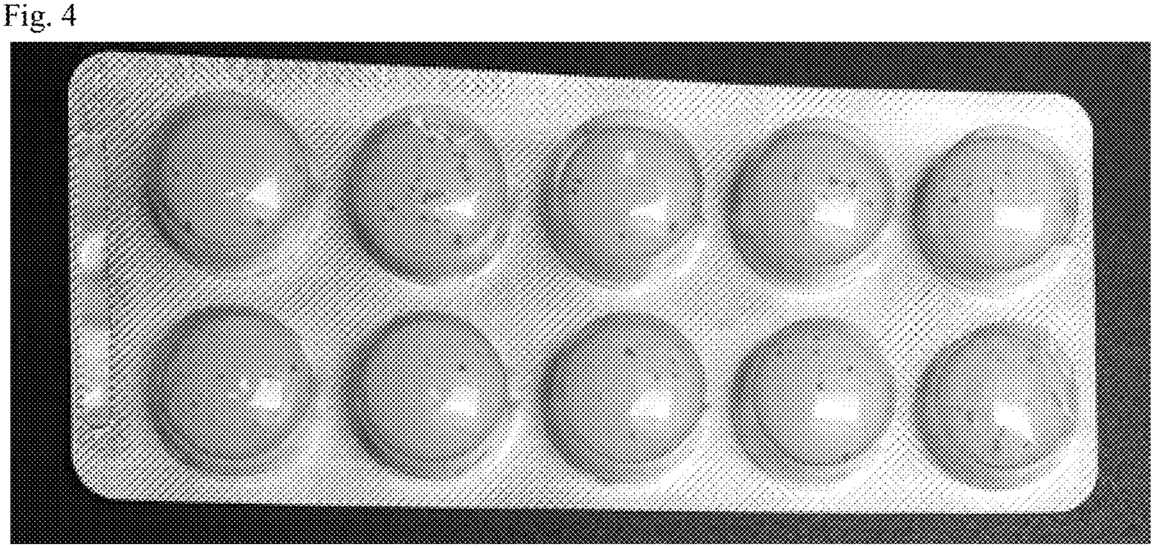
FIG. 4: Example of a final manufactured chewing gum comprising assembled P11-4 per compressed gum description prepared according to Example 1B.
Figure 5:
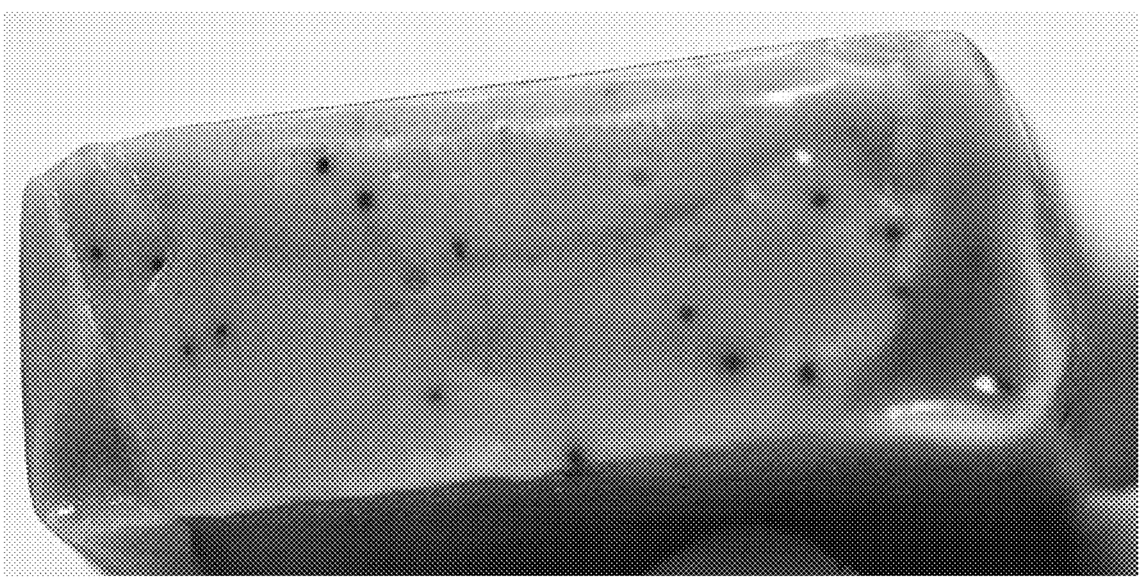
FIG. 5: Cross Section of a Toffee comprising assembled P11-4 prepared according to Example 1A with titration.

Example 1: Preparation of a Dental Care Product of the Invention

A) Preparation of a Toffee of the Invention

After material provision, a computer-based weighing system ensures that all ingredients are precisely weighed for the subsequent cooking process generating the first matrix. The cooking is performed at 100-150° C. under agitation.

In parallel, the pre-mix is prepared. The self-assembling peptide, e.g., P11-4, is weighed into a suitable vessel. Then the powder is transferred under stirring into another vessel containing a basic solvent i.e. water with pH 8 adjusted with 0.1 N NaOH solution. After addition of the self-assembling peptide, the solution is kept for 5 min at basic pH to assure monomeric peptide. Then, with acid preferably phosphoric acid or citric acid 0.1 N, the solution is slowly titrated to pH 6 initiating the self-assembling of the peptide. This results in a slightly opaque solution. The concentration of the peptide may be, e.g., between 20 to 100 g/L.

In order to meet the product requirements, the pre-mix is continually added either during on-line mixing or straight after on-line mixing in the cooling tunnel. Preferably in the cooling phase with a maximum temperature of 85° C. The resulting raw toffee is stretched and formed with a cone roller into rods followed forming by a levelling roller into a bar shape. After this transformation of the shape, the now cooled toffee is cut and on-line wrapped into a wrapper. The wrapped toffees may be packaged or stored as bulk awaiting further packaging.

Alternatively, the bulk can be prepared as followed without titration:

After material provision, a computer-based weighing system ensures that all ingredients are precisely weighed for the subsequent cooking process generating the first matrix. The cooking is performed at 100-150° C. under agitation.

In parallel, the pre-mix is prepared. The self-assembling peptide, e.g., P11-4, is weighed into a suitable vessel. Then the powder is transferred under stirring into another vessel containing an acid solution of preferably phosphoric acid or citric acid at pH 6. If required, the pH is corrected with the corresponding acid. This results in an opaque, yellowish viscous solution. The concentration of the peptide may be, e.g., between 20 to 60 g/L.

In order to meet the product requirements, the pre-mix is continually added either during on-line mixing or straight after on-line mixing in the cooling tunnel. Preferably in the cooling phase with a maximum temperature of 85° C. The resulting raw toffee is stretched and formed with a cone roller into rods followed by a levelling roller into a bar shape. After this transformation of the shape, the now cooled toffee is cut and on-line wrapped into a wrapper. The wrapped toffees may be stored as bulk awaiting further packaging, or packaged.

B) Preparation of a Chewing Gum of the Invention

Prior the material provision, the SAP-matrix is prepared. The self-assembling peptide is weighed into a suitable vessel. Then the powder is transferred under stirring into another vessel containing a basic solvent, i.e., water with pH 8 adjusted with 0.1 N NaOH solution. After addition of the self-assembling peptide, the solution is kept at a basic pH for 5 min to assure monomeric peptide. Then, with acid, preferably phosphoric acid or citric acid 0.1 N, the solution is slowly titrated to pH 6, initiating the self-assembling of the peptide. This results in a slightly opaque solution. The concentration of the peptide may be, e.g., between 20 to 100 g/L. This solution is then dried, e.g., freeze dried or spray dried, conserving the fibrillar structure of the matrix.

After material provision, a computer-based weighing system ensures that all ingredients are precisely weighed for the subsequent mixing procedure. The granulating agent, most preferably sorbitol, the lubricant, e.g., magnesium stearate or talc, etc. is added, and then mixed in a blender. Later, the powder of assembled peptide is added, and the free-flowing powder directly dosed into the pressing equipment.

To increase the usability in terms of taste, a coating may be applied after preparation of the coating bulk, i.e. in a separate vessel. For this a peptide solution may be prepared as discussed above. This solution is then added to the flavours, coloring agents etc. by homogenization and is later used for spray coating of the compressed gums.

After coating, the gums may be directly blistered and sealed, and optionally, further packaged.

Example 2: Acid Erosion Testing

Preparation of the Samples

| Material | |
|---|---|
| Description | Supplier |
| Human Enamel Disks | Tissue Bank |
| 15 ml Falcon tube | Fisher Sci |
| pH Paper | Merck |
| Stop watch | — |
| Shaker | IKA |
| Plasma Sputter Polaron SC7620 | Thermo VG Scientific (Au Plasma) |
| Carbon tape | Thermo |
| SEM SUPRA 40 VP Gemini | Carl Zeiss |
| Phosphate Buffered Saline | Sigma Aldrich |
| Citric acid<br>→ citric acid solution 6% in water | credentis |
| remineralization buffer:<br>2 mM Ca(NO3)2<br>1.2 mM KHPO4;<br>60 mM Tris/HCl.<br>(pH adjusted to 7.4 with 1M KOH) | credentis |
| Artificial Saliva | Sigma Aldrich |
| Blotting paper | VWR |
| Coca Cola | Coca Cola |

Enamel Disk Preparation
- Remove tooth, preferably human, from the refrigerator
  - Tooth should have intact surface
- Blot it dry
- Cut out parts of the enamel
- Store in PBS solution Incubation
- Remove slices from PBS solution
- Rinse under tap water
- Incubate for 48 h in remineralization buffer
- Remove from solution
- Apply enamel slice to artificial teeth of artificial mastication equipment with 2K glue Artificial masticate toffee with or without assembled P11-4 (33 mg/ml) with 3 mL artificial saliva for 5 min
Remove "saliva"
Incubate 1 piece of enamel in "saliva" for 5 min
Remove enamel slice form tooth
Incubate enamel section for 30 min in coca cola
Place the on-blotting paper
Air dry for 24 h SEM Preparation
Place samples on SEM-sample holder on carbon tape
Sputter sample for 30 s in an Au-Plasma under Argon 8*10-2 Pa 30 s @ 20 mA coating with Gold
Analyse the sample in SEM "Carl Zeiss".

Figure 6:
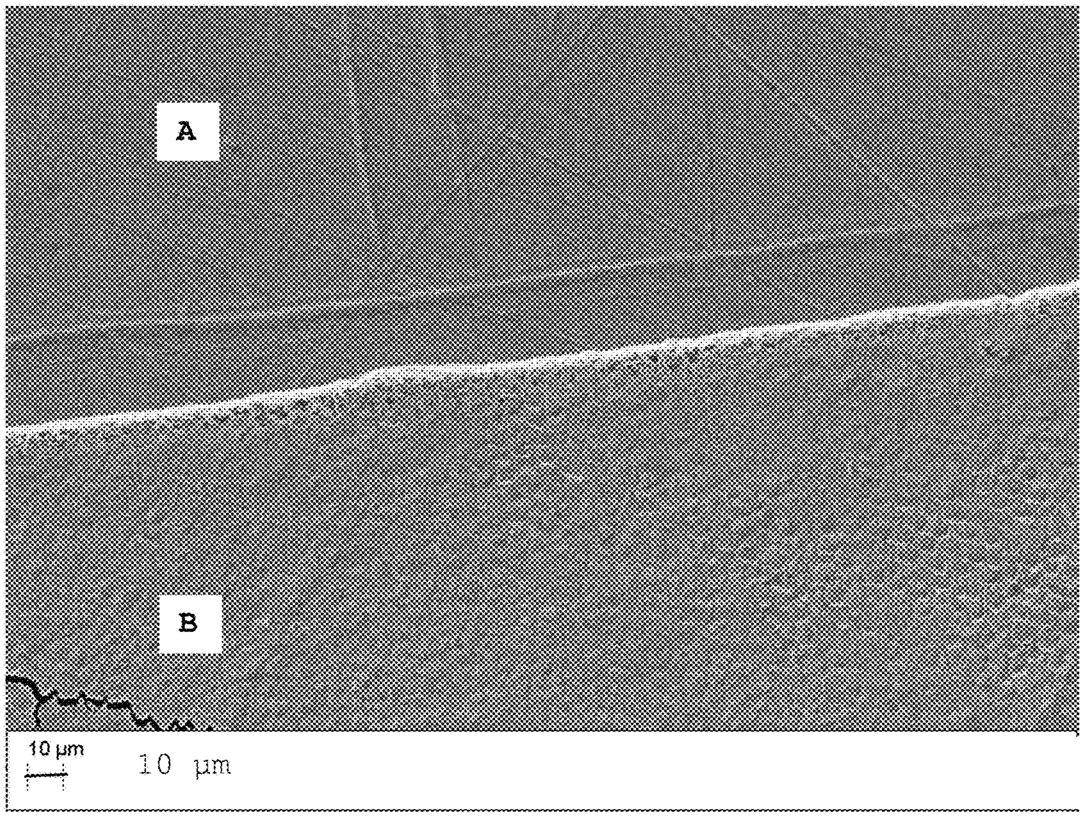
FIG. 6: SEM Picture per example 2 with protective layer. a) intact human enamel (covered with varnish during experiment and removed for inspection) b) exposed human enamel with protective layer after acid erosion experiment showing reduced demineralization compared to FIG. 7 proving the protective effect of the treatment. Magnification: 1000×, Signal: SE2, EHT: 10
Figure 7:
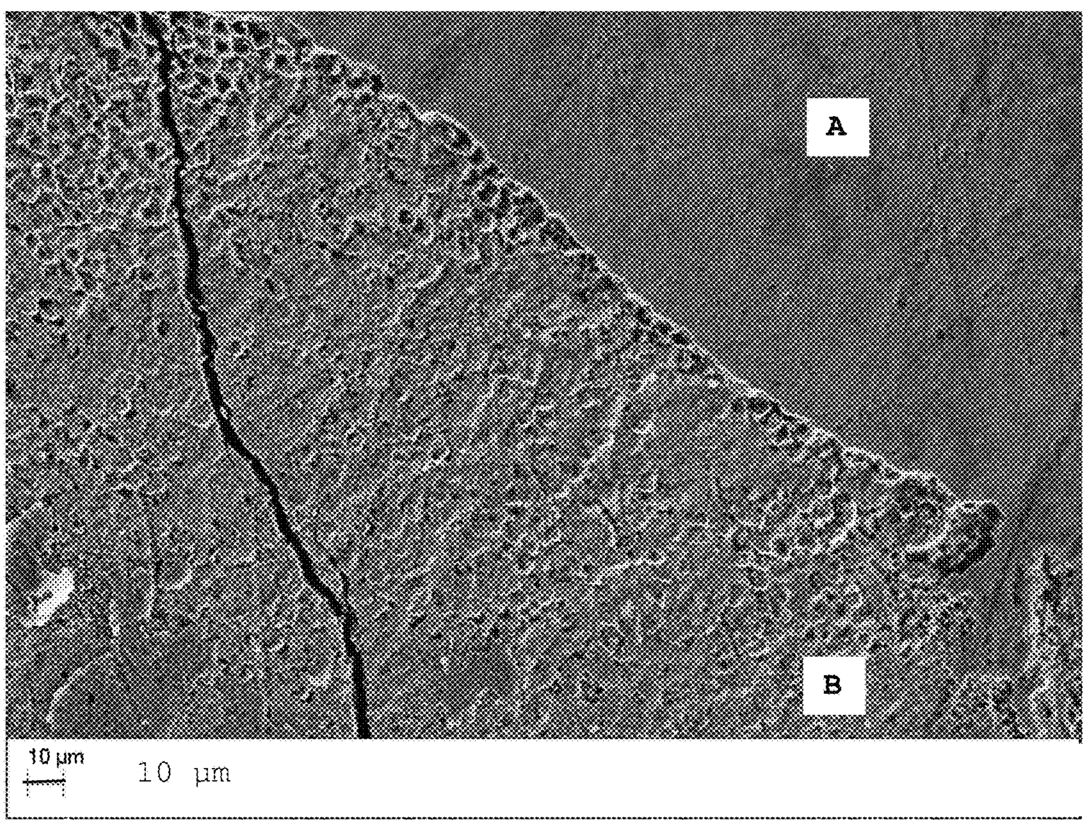
FIG. 7: kVSEM Picture per example 2 without protective layer. a) intact human enamel (covered with varnish during experiment and removed for inspection) b) exposed human enamel without protective layer after acid erosion experiment showing severe demineralization. Magnification: 1000×, Signal: SE2, EHT: 10 kV
Figure 8:
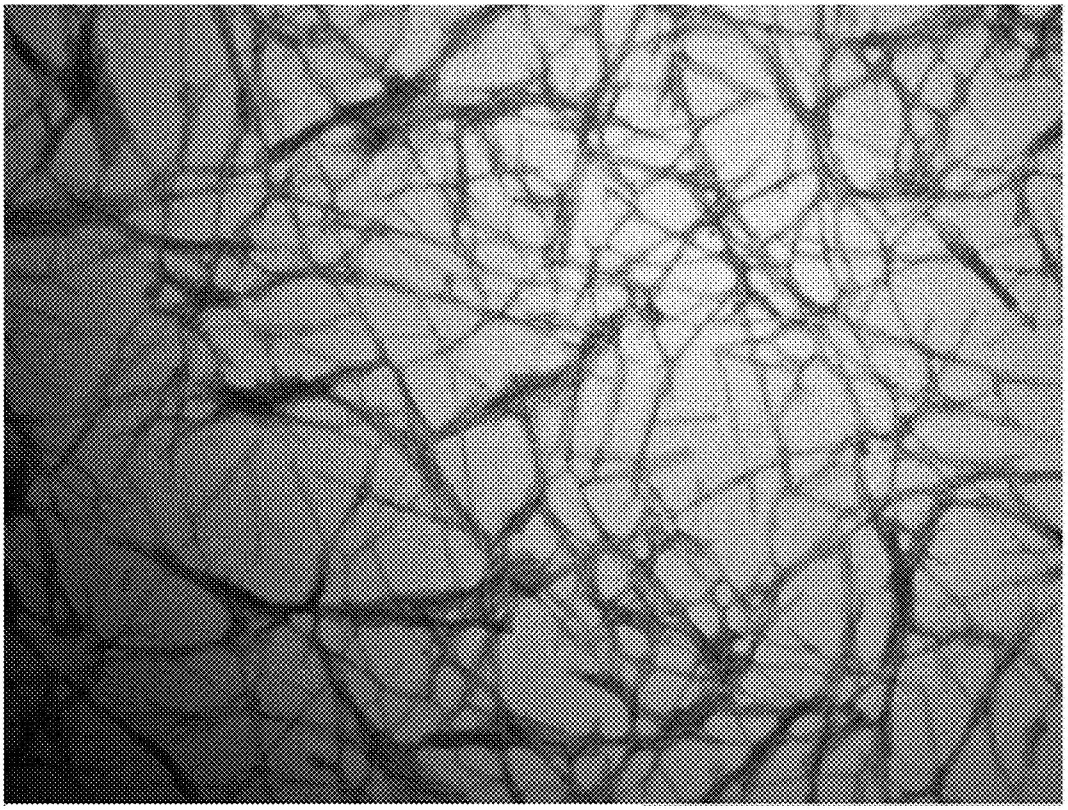
FIG. 8: TEM of Reference assembled P11-4, TEM, 50'000×, 50 kV, AMT
Figure 9:
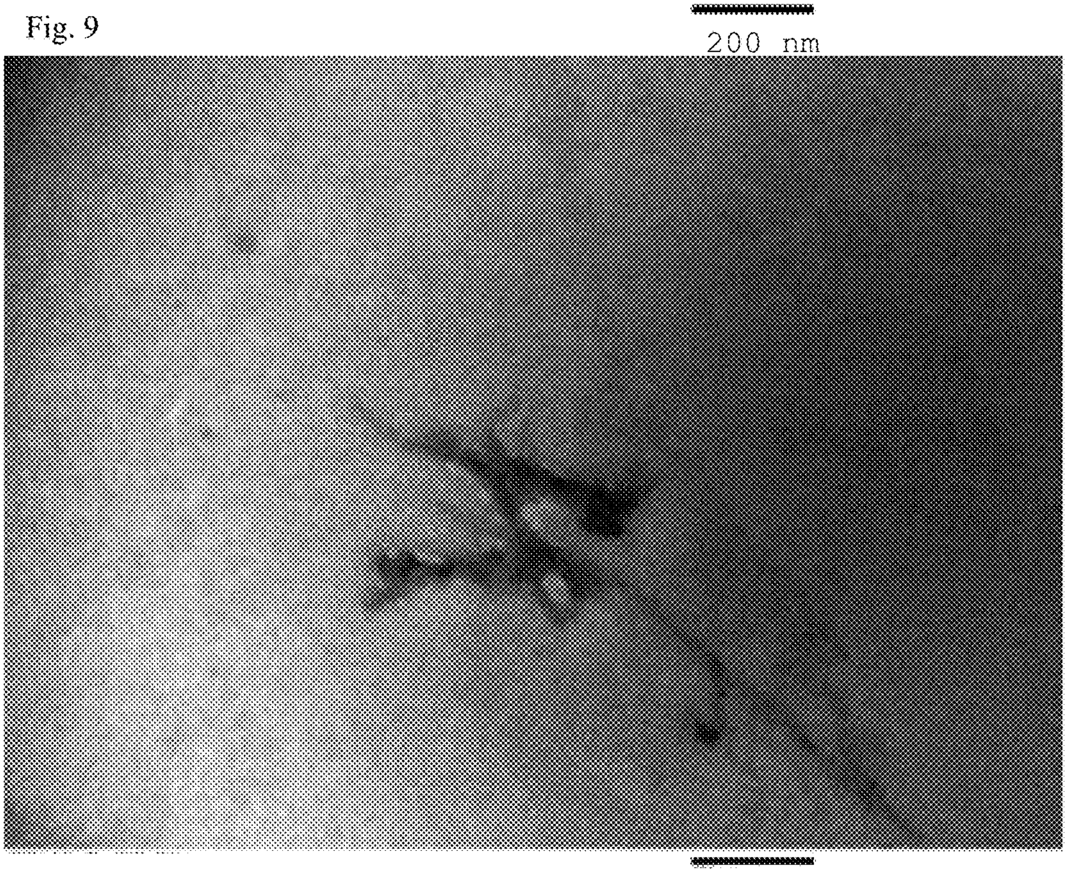
FIG. 9: TEM of artificially chewed toffee-saliva showing distinct fibre bundle of P11-4, cf. example 3. TEM, 50'000×, 50 kV, AMT
Figure 10:
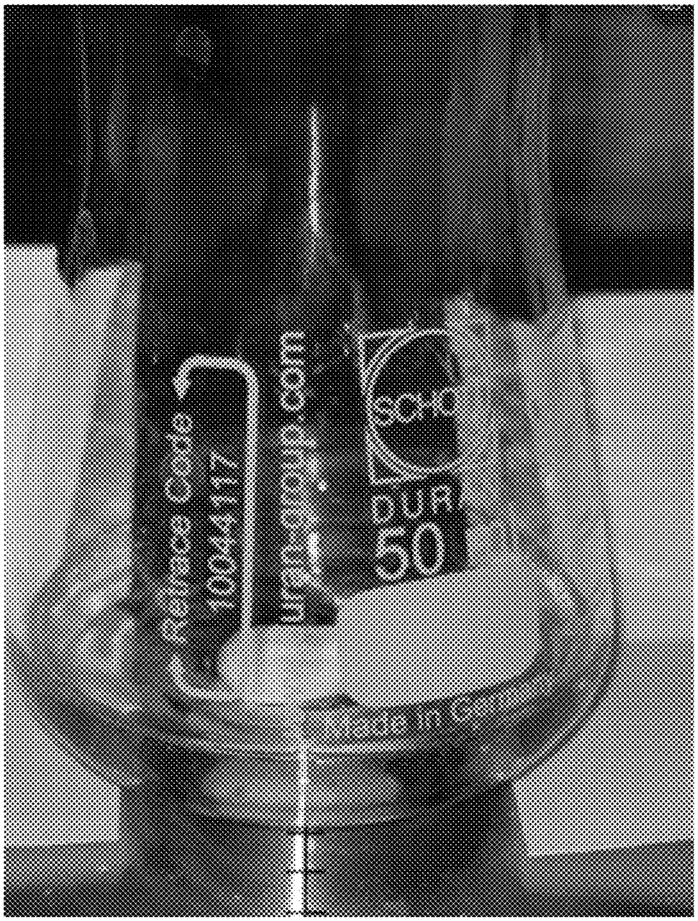
FIG. 10: Solution prepared according to Example 1 with pre-mix and titration. Content is 35 mg*ml-l
Figure 11:
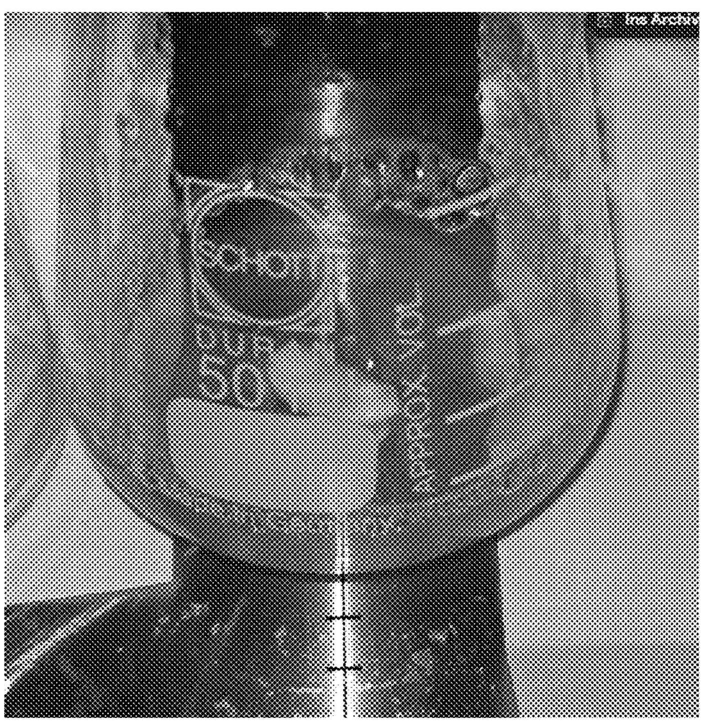
FIG. 11: Solution prepared according to Example 1 without titration resulting in a slightly yellowish, opaque solution. Content is 35 mg*ml/L.
Figure 12:
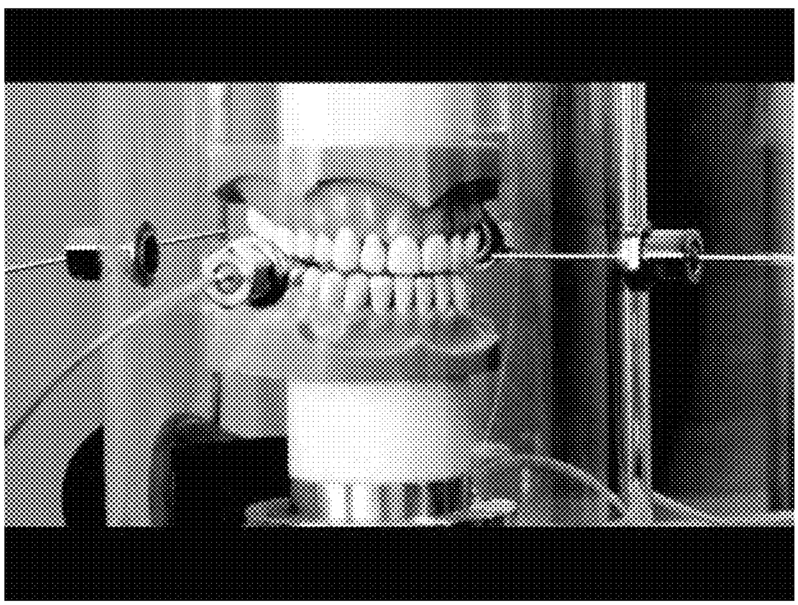
FIG. 12: Apparatus for artificially masticating a dental care product. A similar apparatus is the dental chewing machine of the University of Minnesota, shown, e.g., in https://www.youtube.com/watch?v=LEJymW-g0b0.

Enamel slices were artificially masticated with a toffee comprising assembled P11-4 or blank (saliva only), as described above, then, acid erosion was induced by incubation in coca cola for 30 min. SEM pictures of a representative enamel slices with or without the protective layer formed by mastication of the toffee with assembled P11-4 are shown in FIG. 6 (no protective layer formed) and 7 (with P11-4, with protective layer). Samples having an acid protection/sacrificial layer show lower erosion than those having no protection.

Example 3: Determination of Fibres Eluting from Matrix

| Material |
|---|
| P11-4 assembled as control |
| uL-Pipette Soccorex |
| Cu-TEM Templates 200 Mesh EMS 215-412-810 |
| Uranylacetate 3% EMS 22400-2 Lot: 1B155953/131007 |
| EM900 TEM Zeiss |

Sample:
Place 1 toffee with or without assembled P11-4 (35 mg/ml) in artificial saliva 3 mL (cf. Example 2)
Artificial chew for 5 min in artificial mastication equipment.
Remove supernatant (saliva)

Method TEM
Dilute sample (10 mg/mL) with $H_2O$ at a ratio of 1:63
Place 1 µL of control solution on TEM-grid Sample
Place 20 µL of water on a parafilm
Place gently the TEM Grid with dark site facing upwards on the parafilm, close to the drop
Application of 10 µL sample on TEM carbon coated grids (hexagonal)
10 min incubation
Remove unbound sample with a paper tissue
Put the grid into 3% Uranylacetate solution 20 ul
40 sec incubation
Remove unbound Uranylacetate with a paper tissue
Wash the grid 2 times with distilled water
pipet 5 µL droplet on top of the grid and remove it
Dry it for 20 min at RT
Introduce sample into sample holder for TEM
Analyse @ 50 kV, Vacuum at least 9*10-6 hPa Artificial saliva comprised assembled fibers of self-assembling peptide P11-4 after mastication of a toffee of the invention, i.e., the assembled self-assembling peptide maintains its assembled form after integration in the base of the toffee and after extraction from the same by mastication. This allows for formation of the protective sacrificial layer on the tooth that protects it from erosion.

Example 4: Comparison of the Protective Effects of Monomeric and Assembled Self-Assembling Peptide Against Acid Erosion The aim of this study was to determine the protective effect of polymeric self-assembling peptide compared to monomeric self-assembling peptide, based on an exemplary experiment with toffees.

Since the availability of human teeth is limited, an alternative model has been established by using chicken eggs as the replacement for the human enamel for erosion testing. Even though chicken eggs are made of calcium carbonate rather than calcium phosphate as human teeth, the model is suitable to show a protective effect against acidic attack. The calcium carbonate structure of the chicken egg with is palisade structure resembles the crystal structure of calcium phosphate in the human teeth. Further, human teeth also contains a share of calcium carbonate (~4%) (Klimuszko et al. 2018 Odontology 106:369-376).

An acidic attack in tooth erosion may be caused by acetic acid, phosphoric acid or other organic or inorganic acids. For translational purposes, Coca Cola® was used, one of the widely consumed beverages substantially decreasing the oral pH— 1.7 billion servings of Coca Cola are used daily worldwide.

The hypothesis tested in this semi-quantitative acid-erosion model is if the eggshell is better protected by the polymeric or aggregated self-assembling peptide P11-4 compared to the monomeric self-assembling peptide P11-4.

To prove this hypothesis, two sets of toffees were created and compared. The basic formulation was identical, however, the peptide was added as a monomer to the monomeric form and as a hydrogel in the polymeric form. The material was added during the toffee production process after the heating step, but before use of the mixing rods.

| Material and Methods | | |
|---|---|---|
| Curodont ™Toffees Monom. | Credentis ag | 194322-02 (Monomeric) |
| Curodont ™Toffees Polym. | Credentis ag | 194-PM-X (Polymeric) (not yet commercially available) |
| Balance | Mettler Toledo | PM300 |
| Rotating Wheel | Snijders | Rotator 34528 |
| Pipette | Socroex | 10-100 µL |
| Digital Microscope | | |
| Centrifugation Tube 15 ml | VWR | |
| Crystallizing Dish 300 ml | Duran | |
| Isotonic NaCl 0.9% | Labor Bichsel | L170192 |
| Chicken Eggs, fresh | Volg | |
| Food Colorant | Dr. Oetker | |
| Maybelline Express Finish 40 s | Maybelline | |
| Acetone | Sigma | |
| ImageJ | 1.53e | |

Toffees were cut and 4.2 g weighed in 15 mL centrifugation tube. 3 mL of isotonic NaCl solution, mimicking the natural saliva and volume present in oral cavity, were added and the samples placed over night in a rotating wheel.

Raw chicken eggs were carefully opened on one side and the egg white and yolk discarded. The empty chicken eggs were then washed and dried. Following drying, on two places of the egg, a grid was first drawn with a fine pencil and then coated with nail varnish, see FIG. 13B.

After the nail varnish had dried, the eggs were colored with blue food dye "brilliant blue FCF" for better visibility by applying the colour directly on the chicken egg with a sponge. With a clean sponge, excess colour was then removed, resulting in an even distribution of the colour, see FIG. 13C. The partially colored eggs were then dried at 40° C. for 2 hours.

Figure 13:
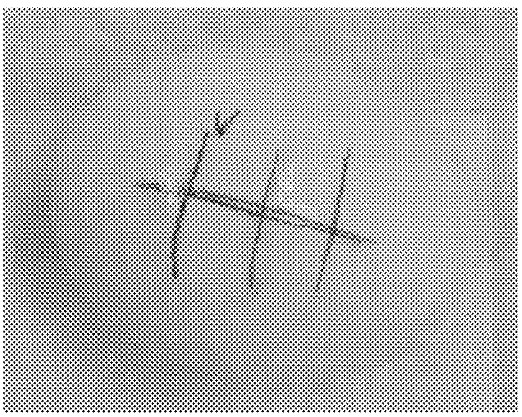
FIG. 13: Comparison of the protective effect of monomeric and polymeric self-assembling peptide. A Sample Distribution on egg-grid. Top left original, untreated surface protected by varnish, top right: sample 1 with polymerized self-assembling peptide. Bottom left-sample 2 with monomeric self-assembling peptide, bottom right unprotected surface. B empty chicken egg with drawn grid, coated with Maybelline express finish 40 s. The top square, indicated with a "V" was coated completely with nail varnish to present an undisturbed, native surface. The three remaining squares are kept blank for the following investigation. C Colored chicken egg with the grid for sample allocation. the slightly whitish appearance on top left is due to the protection by varnish and therefore not resulting in good adhesion of the color. D Incubation of eggshell in Coca Cola® in a crystallizing dish. The site coated with the samples was balanced with 2 g of lead to assure proper balancing and full contact to the acid of the liquid. E Egg 3 after 5 min incubation in Coca Cola® after rinsing with water. Top left: area protected with Varnish "V", top right: Polymeric P11-4 "P", bottom left: monomeric P11-4 "M", bottom right: control "C". F Example of a black-white converted surface including area to be analyzed (thin line). G Results of "Analyze Particle" of ImageJ output. A high percentage of protected surface is seen in the erosion model with the samples with polymeric self-assembling peptide, and intermediate protection with monomeric self-assembling peptide, and most erosion is seen without protection, i.e., with the control. Of note, the colour did not adhere to the varnish, which explains that there is 0% black area shown for the varnish samples.
Figure 13:
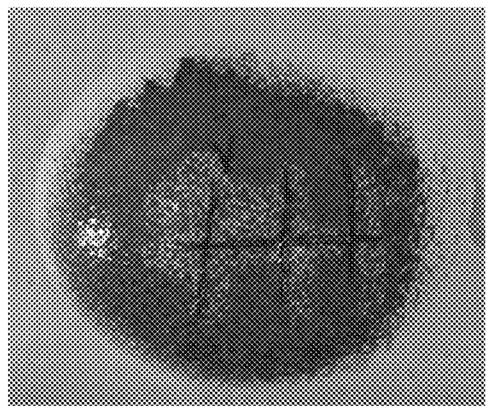
Figure 13:
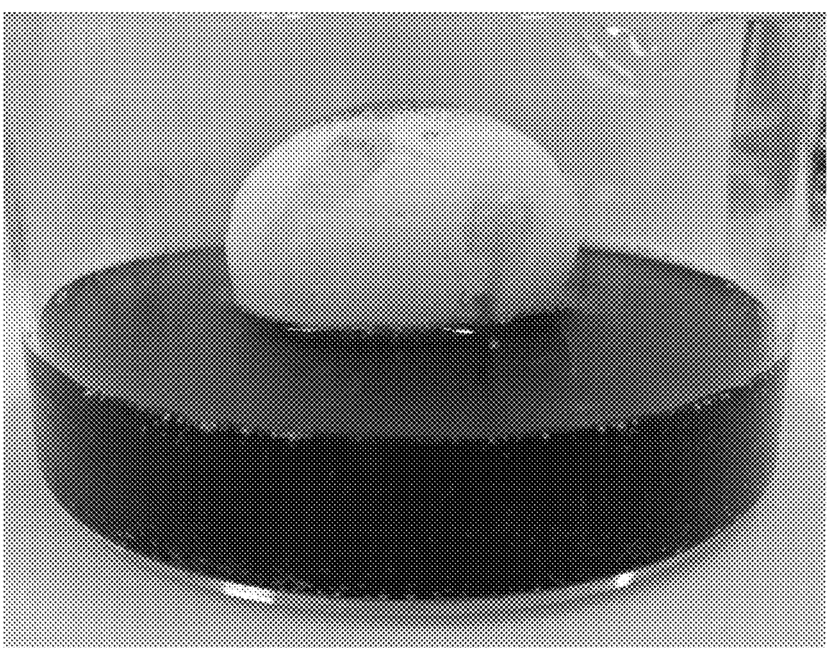
Figure 13:
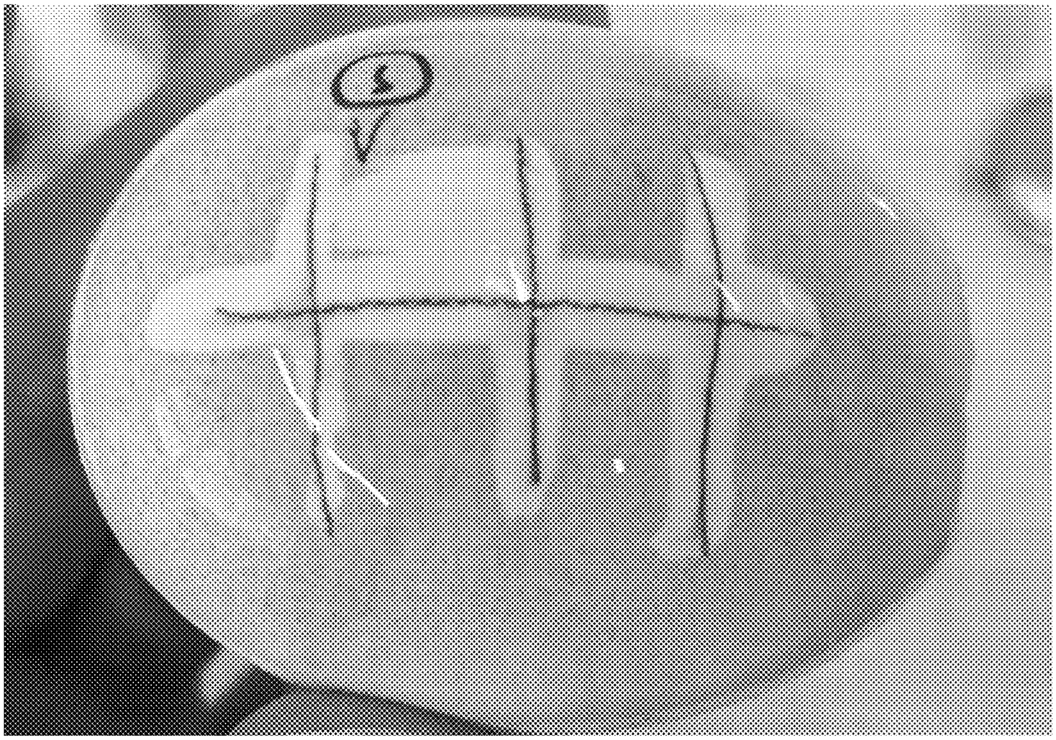
Figure 13:
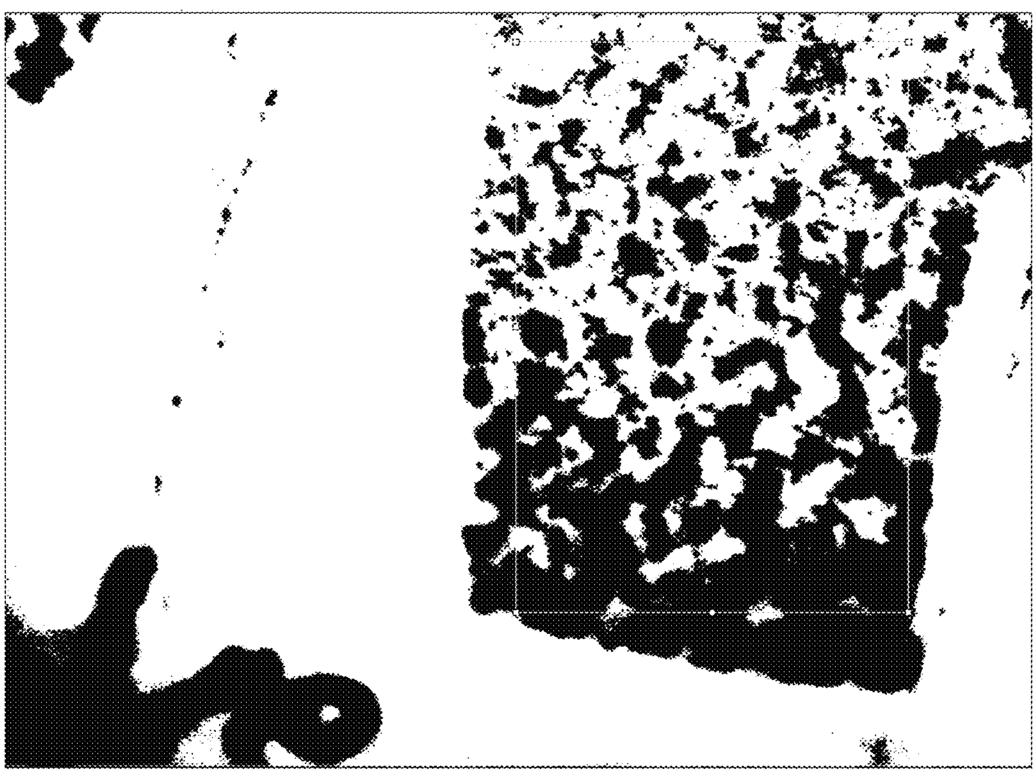
Figure 13:
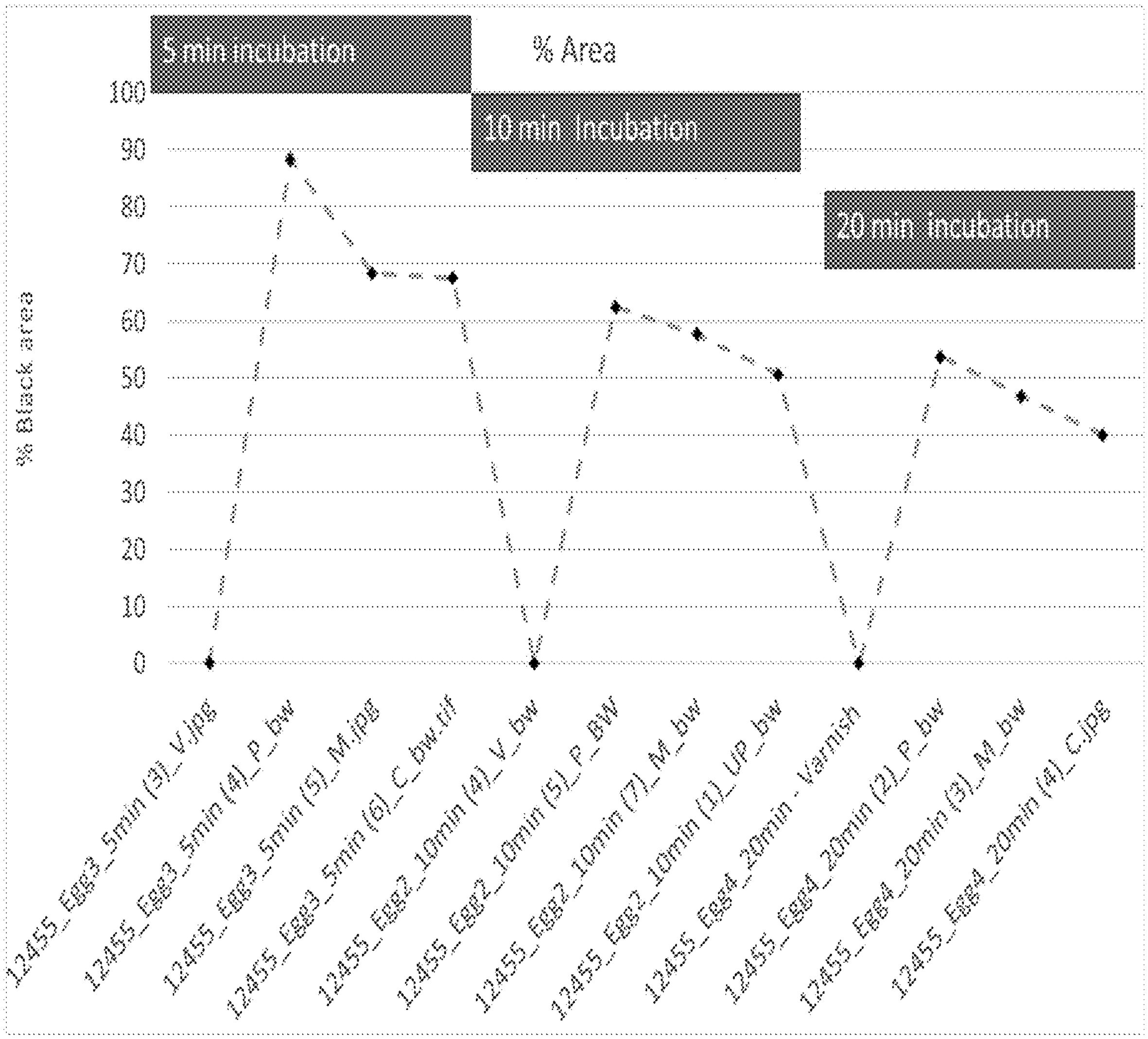

After drying, the samples were allocated as defined in FIG. 13A

25 μL of the extracted sample or control was placed with a pipette on the dried egg surface and let soak into it. The step was repeated twice to assure full covering of the square.

Following drying at 40° C. for 1 h, the egg shell was placed in 21° C. Coca Cola (pure) and incubated for 5, 10 and 20 min as per FIG. 13D.

After incubation, the egg shell was removed (FIG. 13E), and washed with water, followed by removal of the varnish with Acetone. The egg shell was then air dried.

The areas where the samples had been applied were then investigated with a digital USB microscope for the distribution of the dye. In areas where the acid liquid eroded the egg shell, less colour was found on the surface, as the colour erodes with the surface of the shell.

The pictures were opened with ImageJ each picture selected and converted to a binary picture, i.e., darker areas of the shell with intense blue colour, where the shell had been protected, were converted to black, and lighter regions, where the shell had eroded were converted to white. An exemplary picture is shown in FIG. 13F. Within the grid, squares as big as possible were analyzed with the "Analyze-Particle" function.

It should be noted that the nail varnish prevents access of the dye to the surface of the egg shell, so that the colour is lost after washing even though the shell is optimally protected under the varnish.

Results

TABLE 2

Computed data obtained by ImageJ Particle Analysis. As per the grid definition, the "V" stands for varnish (native structure), "P" for polymeric Self-assembling Peptide, "M" for monomeric Self-assembling Peptide and "C" for unprotected surface.

| ID | count | Total Area | Average Size | % Area |
|---|---|---|---|---|
| 12455_Egg3_5 min (3)_V.jpg | 18 | 102 | 5.667 | 0.007 |
| 12455_Egg3_5 min (4)_P_bw | 741 | 1011800 | 1365.452 | 88.384 |
| 12455_Egg3_5 min (5)_M.jpg | 310 | 130124 | 419.755 | 68.398 |
| 12455_Egg3_5 min (6)_C_bw.tif | 386 | 213628 | 553.44 | 67.561 |
| 12455_Egg2_10 min (4)_V_bw | 5 | 8 | 1.6 | 6.59E−04 |
| 12455_Egg2_10 min (5)_P_BW | 1450 | 580723 | 400.499 | 62.515 |
| 12455_Egg2_10 min (7)_M_bw | 3425 | 755952 | 220.716 | 57.699 |
| 12455_Egg2_10 min (1)_C_bw | 1587 | 461484 | 290.79 | 50.656 |
| 12455_Egg4_20 min - Varnish | missing | | | |
| 12455_Egg4_20 min (2)_P_bw | 614 | 660990 | 1076.531 | 53.782 |
| 12455_Egg4_20 min (3)_M_bw | 1450 | 546241 | 376.718 | 46.758 |
| 12455_Egg4_20 min (4)_C.jpg | 6501 | 956391 | 147.114 | 39.988 |

Conclusions

The obtained data confirms the hypothesis that polymeric self-assembling peptide P11-4 "P" leads to better erosion protection compared to monomeric self-assembling peptide P11-4 "M". The effect is highest with a short time of incubation of 5 min, where the polymeric material protects roughly 20% more of the area compared to the monomeric form and the control "C", FIG. 13G. With longer incubation times, the effect as well as the difference between the values becomes smaller, but the polymeric self-assembling peptide still has a better protective effect than monomeric self-assembling peptide, which is still more protective than the control.

EMBODIMENTS OF THE INVENTION

The invention provides

1. A dental care product comprising (i) self-assembling peptides comprising the sequence of SEQ ID NO: 21, wherein the self-assembling peptides are essentially present in the dental care product in assembled form (in particular, at least 80%, preferably at least 90% or at least 95%), and (ii) a pharmaceutically acceptable basis, wherein the dental care product is an essentially solid product selected from the group consisting of chewing gum, soft chew, gelatin gum, chewy candy, chew toy, toffee, lozenge and tablet, and wherein the dental care product is not abrasive.

2. The dental care product of embodiment 1, wherein self-assembling peptides in assembled form are embedded in the pharmaceutically acceptable basis, preferably, in a gum base.

3. The dental care product of embodiment 2, wherein the gum base comprises polymers, plasticizers and/or resins.

4. The dental care product of embodiment 2, wherein the gum base comprises a) synthetic ingredients selected from the group consisting of butadiene-styrene rubber, isobutylene-isoprene copolymer (butyl rubber), paraffin (produced via the Fischer-Tropsch process), petroleum way, petroleum wax synthetic, polyisobutylene polyvinyl acetate, polyisobutadiene and isobutylene-isoprene copolymers, low molecular weight elastomers such as polybutene, polybutadiene and polyisobutylene, vinyl polymeric elastomers such as polyvinyl acetate, polyethylene, vinyl copolymeric elastomers such as vinyl acetate/vinyl laurate, vinyl acetate/vinyl Stearate, ethylene/vinyl acetate, polyvinyl alcohol or mixtures thereof, and/or b) natural ingredients selected from the group consisting of chicle, chiquibul, crown gum, gutta hang kang, massaranduba balata, massaranduba chocolate, nispero, rosdinha, Venezuelan chicle, jelutong, leche saspi, pendare, perillo, leche de vaca, niger gutta, tuno, chilte and natural rubber.

5. The dental care product of any of the preceding embodiments, comprising gelatin, albumen, lecithin, pectin or starch.

6. The dental care product of any of the preceding embodiments, wherein the concentration of self-assembling peptides is 0.1-500 mg/kg, preferably, about 5-15 mg/kg.

The dental care product of any of the preceding embodiments, wherein said peptide comprises the sequence of SEQ ID NOs: 22.

8. The dental care product of any of the preceding embodiments, wherein said peptide comprises the sequence of SEQ ID NOs: 23.

9. The dental care product of any of the preceding embodiments, wherein said peptide comprises the sequence of SEQ ID NOs: 24.

10. The dental care product of any of the preceding embodiments, wherein said peptide comprises the sequence of SEQ ID NOs: 25.

11. The dental care product of any of the preceding embodiments, wherein said peptide comprises the sequence of SEQ ID NOs: 26.

12. The dental care product of any of the preceding embodiments, wherein said peptide comprises the sequence of any one of SEQ ID NOs: 1-20.

13. The dental care product of any of the preceding embodiments, wherein said self-assembling peptides comprise a sequence having at least 80% sequence identity to one of the sequences of SEQ ID NOs: 1, 2 or 20, wherein said peptide preferably comprises the sequence of SEQ ID NO: 1.

14. The dental care product of embodiment 13, wherein said self-assembling peptides comprise a sequence having at least 80% sequence identity to SEQ ID NO: 1, wherein said peptide preferably comprises the sequence of SEQ ID NO: 1.

15. The dental care product of embodiment 13, wherein said self-assembling peptides comprise a sequence having at least 80% sequence identity to SEQ ID NO: 3, wherein said peptide preferably comprises the sequence of SEQ ID NO: 3.

16. The dental care product of embodiment 13, wherein said self-assembling peptides comprise a sequence having at least 80% sequence identity to SEQ ID NO: 20, wherein said peptide preferably comprises the sequence of SEQ ID NO: 20.

17. The dental care product of any of embodiments 1-15, wherein said peptide is capable of undergoing self-assembly at a pH below 7.5.

18. The dental care product of any of embodiments 1-6, 12 or 16, wherein said peptide is capable of undergoing self-assembly at a pH above 7.5.

19. The dental care product of any of the preceding embodiments does not comprise 0.4 wt % or more of mineral particles having a size of at least 0.1 μm.

20. The dental care product of any of the preceding embodiments, wherein the dental care product further comprises a) a polyol such as xylitol, erythritol or sorbitol, preferably, xylitol.

21. The dental care product of any of the preceding embodiments, wherein the dental care product further comprises b) a phosphate such as sodium phosphate calcium phosphate, e.g. hydroxyapatite, 22. The dental care product of any of the preceding embodiments, wherein the dental care product further comprises c) a pyrophosphate.

23. The dental care product of any of the preceding embodiments, wherein the dental care product further comprises d) a pH controlling agent such as sodium bicarbonate or urea.

24. A process for preparing a dental care product of any of embodiments 1-23, comprising steps of a) providing a matrix of assembled self-assembling peptide, b) providing a pharmaceutically acceptable basis, preferably, a gum base, wherein steps a) and b) can be carried out in any order, and c) homogenizing the matrix of assembled self-assembling peptide and the pharmaceutically acceptable basis, preferably, the gum base, optionally, together with other ingredients, d) forming the dental care product and, e) optionally, packaging the dental care product.

25. The process of embodiment 24, wherein the matrix of step a is prepared drying a solution having a pH at which the self-assembling peptide is assembled (e.g., a pH below 7.5 for a peptide of SEQ ID NO: 22), e.g., by spray drying, lyophilisation or evaporation.

26. The dental care product of any of embodiments 1-23, obtainable by a process of any of embodiments 22 or 23.

27. A dental care product of any of embodiments 1-23 or 26 for use in reducing demineralisation of a tooth surface of a subject with demineralised teeth, preferably, for reducing further demineralisation of a tooth surface of a subject with demineralised teeth.

28. The dental care product for use of embodiment 27, wherein the subject has a disease or condition associated with reduced remineralisation of teeth.

29. The dental care product for use of any of embodiments 27 or 28, wherein the subject has xerostomia, hyopsalivation, bruxism, dentine hypersensitivity and/or tooth erosion.

30. The dental care product for use of any of embodiments 27-29, wherein the subject has xerostomia.

31. The dental care product for use of embodiment 30, wherein the xerostomia is associated with hyposalivation.

32. The dental care product for use of any of embodiments 27-31, wherein the subject has hyopsalivation.

33. The dental care product for use of any of embodiments 27-32, wherein the subject has bruxism.

34. The dental care product for use of any of embodiments 27-33, wherein the subject has tooth erosion.

35. The dental care product for use of embodiment 34, wherein the subject has gastroesophageal reflux disease.

36. The dental care product for use of any of embodiments 27-35, wherein the subject has dentine hypersensitivity.

37. The dental care product for use of any of embodiments 27-36, wherein the subject has a clinical oral dryness scale of at least 1, preferably, at least 4 or at least 7 on the Challacombe Scale.

38. The dental care product for use of any of embodiments 27-37, wherein the dental care product is administered to the mouth of the subject, wherein the dental care product preferably is to be maintained in the mouth for at least 3 min.

39. The dental care product for use of any of embodiments 26-37, wherein the dental care product is to be masticated by the subject, wherein, preferably, five minutes mastication increase the salivary flow by a factor of at least 10.

40. The dental care product for use of any of embodiments 27-39, wherein, upon mastication, the gum base cleans the tooth surface, and the matrix of assembled self-assembling peptide provides a film on the tooth surface that reduces or prevents further demineralisation of the tooth surface.

41. The dental care product for use of any of embodiments 27-40, wherein the dental care product is administered at least once a day, preferably, at least twice a day.

42. The dental care product for use of any of embodiments 27-41, wherein the dental care product is administered after a meal or snack, optionally, instead of brushing the teeth.

43. The dental care product for use of any of embodiments 27-42, wherein the dental care product is administered after waking to reduce xerostomia.

44. The dental care product for use of any of embodiments 27-43, wherein the dental care product reduces the incidence, and preferably, prevents caries.

45. The dental care product for use of any of embodiments 27-44, wherein the dental care product re-duces pain associated with dentine hypersensitivity.

The invention claimed is:

1. A method for reducing further demineralisation of a tooth surface of a subject with demineralised teeth, wherein the subject has a disease or condition associated with reduced remineralisation of teeth selected from the group consisting of xerostomia, hyposalivation, bruxism, dentine hypersensitivity and/or tooth erosion, the method comprising orally administering a dental care product to the mouth of the subject for at least 3 minutes, wherein the dental care product does not comprise 0.4 wt % or more of mineral particles having a size of at least 0.1 μm, is non-abrasive, and comprises (i) self-assembling peptides comprising the sequence of SEQ ID NO: 21, wherein the self-assembling peptides are essentially present in the dental care product in assembled form, and (ii) a pharmaceutically acceptable gum basis, wherein the dental care product is an essentially solid product selected from the group consisting of chewing gum, soft chew, toffee, gelatin gum, chewy candy, chew toy, lozenge, or tablet.

2. The method of claim 1, wherein the subject has xerostomia associated with hyposalivation.

3. The method of claim 1, wherein the dental care product is to be masticated by the subject, wherein, five minutes mastication increase the salivary flow by a factor of at least 10.

4. The method of claim 1, wherein, upon mastication, the pharmaceutically acceptable gum basis cleans the tooth surface, and the matrix of assembled self-assembling peptide provides a film on the tooth surface that reduces or prevents further demineralisation of the tooth surface.

5. The method of claim 1, wherein the dental care product reduces the incidence of caries.

6. The method of claim 1, wherein the pharmaceutically acceptable basis is a gum base comprising ingredients selected from the group comprising polymers, plasticizers and/or resins.

7. The method of claim 1, wherein the concentration of self-assembling peptides is 5-15 mg/kg.

8. The method of claim 1, wherein said peptide comprises the sequence of SEQ ID NO: 1.

9. The method of claim 1, wherein self-assembling peptides in assembled form are embedded in the pharmaceutically acceptable gum basis.

10. The method of claim 9, wherein the pharmaceutically acceptable gum basis comprises a) synthetic ingredients selected from the group consisting of butadiene-styrene rubber, isobutylene-isoprene copolymer, paraffin, petroleum way, petroleum wax synthetic, polyisobutylene polyvinyl acetate, polyisobutadiene and isobutylene-isoprene copolymers, low molecular weight elastomers such as polybutene, polybuta-diene and polyisobutylene, vinyl polymeric elastomers such as polyvinyl acetate, polyethylene, vinyl copolymeric elastomers such as vinyl acetate/vinyl laurate, vinyl acetate/vinyl Stearate, ethylene/vinyl acetate, polyvinyl alcohol or mixtures thereof, and/or b) natural ingredients selected from the group consisting of chicle, chiquibul, crown gum, gutta hang kang, massaranduba balata, massaranduba chocolate, nispero, rosdinha, Venezuelan chicle, jelutong, leche saspi, pendare, perillo, leche de vaca, niger gutta, tuna, chilte and natural rubber.

11. The method of claim 1, wherein the dental care product comprises gelatin, pectin, albumen, lecithin, maltitol/sorbitol or starch.

12. The method of claim 1, wherein the concentration of self-assembling peptides in the dental care product is 0.1-5000 mg/kg.

13. The method of claim 1, wherein said peptide comprises the sequence of SEQ ID NO: 22.

14. The method of claim 1, wherein said self-assembling peptides comprise a sequence having at least 80% sequence identity to one of the sequences of SEQ ID NOs: 1, 3 or 20.

15. The method of claim 1, wherein the dental care product comprises at least one further ingredient selected from the group comprising a) a polyol selected from the group comprising xylitol, erythritol and sorbitol, b) a salt selected from the group comprising calcium carbonate and phosphate, and having a MOSH hardness of less than 3, c) a pyrophosphate, and d) a pH controlling agent.

* * * * *

SEQUENCE LISTING

```
<160> NUMBER OF SEQ ID NOS: 26

<210> SEQ ID NO 1
<211> LENGTH: 11
<212> TYPE: PRT
<213> ORGANISM: Artificial Sequence
<220> FEATURE:
<223> OTHER INFORMATION: self-assembling peptide P11-4

<400> SEQUENCE: 1

Gln Gln Arg Phe Glu Trp Glu Phe Glu Gln Gln
1               5                   10


<210> SEQ ID NO 2
<211> LENGTH: 11
<212> TYPE: PRT
<213> ORGANISM: Artificial Sequence
<220> FEATURE:
<223> OTHER INFORMATION: self-assembling peptide
<220> FEATURE:
<221> NAME/KEY: MOD_RES
<222> LOCATION: (3)..(3)
<223> OTHER INFORMATION: Orn
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (7)..(7)
<223> OTHER INFORMATION: Orn

<400> SEQUENCE: 2

Gln Gln Xaa Phe Xaa Trp Xaa Phe Gln Gln Gln
1               5                   10


<210> SEQ ID NO 3
<211> LENGTH: 11
<212> TYPE: PRT
<213> ORGANISM: Artificial Sequence
<220> FEATURE:
<223> OTHER INFORMATION: self-assembling peptide P11-8
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (7)..(7)
<223> OTHER INFORMATION: Orn

<400> SEQUENCE: 3

Gln Gln Arg Phe Xaa Trp Xaa Phe Glu Gln Gln
1               5                   10


<210> SEQ ID NO 4
<211> LENGTH: 11
<212> TYPE: PRT
<213> ORGANISM: Artificial Sequence
<220> FEATURE:
```

-continued

```
<223> OTHER INFORMATION: self-assembling peptide

<400> SEQUENCE: 4

Gln Gln Arg Phe Gln Trp Gln Phe Glu Gln Gln
1               5                   10


<210> SEQ ID NO 5
<211> LENGTH: 11
<212> TYPE: PRT
<213> ORGANISM: Artificial Sequence
<220> FEATURE:
<223> OTHER INFORMATION: self-assembling peptide

<400> SEQUENCE: 5

Gln Gln Glu Phe Glu Trp Glu Phe Glu Gln Gln
1               5                   10


<210> SEQ ID NO 6
<211> LENGTH: 10
<212> TYPE: PRT
<213> ORGANISM: Artificial Sequence
<220> FEATURE:
<223> OTHER INFORMATION: self-assembling peptide
<220> FEATURE:
<221> NAME/KEY: MOD_RES
<222> LOCATION: (3)..(3)
<223> OTHER INFORMATION: Orn
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (9)..(9)
<223> OTHER INFORMATION: Orn

<400> SEQUENCE: 6

Gln Gln Xaa Phe Xaa Trp Xaa Phe Xaa Gln
1               5                   10


<210> SEQ ID NO 7
<211> LENGTH: 11
<212> TYPE: PRT
<213> ORGANISM: Artificial Sequence
<220> FEATURE:
<223> OTHER INFORMATION: self-assembling peptide

<400> SEQUENCE: 7

Glu Gln Glu Phe Glu Trp Glu Phe Glu Gln Glu
1               5                   10


<210> SEQ ID NO 8
<211> LENGTH: 11
<212> TYPE: PRT
<213> ORGANISM: Artificial Sequence
<220> FEATURE:
<223> OTHER INFORMATION: self-assembling peptide

<400> SEQUENCE: 8

Gln Gln Glu Phe Glu Trp Glu Phe Glu Gln Gln
1               5                   10


<210> SEQ ID NO 9
<211> LENGTH: 11
<212> TYPE: PRT
```

-continued

<213> ORGANISM: Artificial Sequence
<220> FEATURE:
<223> OTHER INFORMATION: self-assembling peptide

<400> SEQUENCE: 9

Glu Ser Glu Phe Glu Trp Glu Phe Glu Ser Glu
1 5 10

<210> SEQ ID NO 10
<211> LENGTH: 11
<212> TYPE: PRT
<213> ORGANISM: Artificial Sequence
<220> FEATURE:
<223> OTHER INFORMATION: self-assembling peptide
<220> FEATURE:
<221> NAME/KEY: MOD_RES
<222> LOCATION: (3)..(3)
<223> OTHER INFORMATION: Orn
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (9)..(9)
<223> OTHER INFORMATION: Orn

<400> SEQUENCE: 10

Gln Gln Xaa Phe Xaa Trp Xaa Phe Xaa Gln Gln
1 5 10

<210> SEQ ID NO 11
<211> LENGTH: 11
<212> TYPE: PRT
<213> ORGANISM: Artificial Sequence
<220> FEATURE:
<223> OTHER INFORMATION: self-assembling peptide
<220> FEATURE:
<221> NAME/KEY: MOD_RES
<222> LOCATION: (1)..(1)
<223> OTHER INFORMATION: Orn
<220> FEATURE:
<221> NAME/KEY: MOD_RES
<222> LOCATION: (3)..(3)
<223> OTHER INFORMATION: Orn
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (9)..(9)
<223> OTHER INFORMATION: Orn
<220> FEATURE:
<221> NAME/KEY: MOD_RES
<222> LOCATION: (11)..(11)
<223> OTHER INFORMATION: Orn

<400> SEQUENCE: 11

Xaa Gln Xaa Phe Xaa Trp Xaa Phe Xaa Gln Xaa
1 5 10

<210> SEQ ID NO 12
<211> LENGTH: 11
<212> TYPE: PRT

-continued

<213> ORGANISM: Artificial Sequence
<220> FEATURE:
<223> OTHER INFORMATION: self-assembling peptide
<220> FEATURE:
<221> NAME/KEY: MOD_RES
<222> LOCATION: (3)..(3)
<223> OTHER INFORMATION: Orn
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (7)..(7)
<223> OTHER INFORMATION: Orn
<220> FEATURE:
<221> NAME/KEY: MOD_RES
<222> LOCATION: (9)..(9)
<223> OTHER INFORMATION: Orn

<400> SEQUENCE: 12

Ser Ser Xaa Phe Xaa Trp Xaa Phe Xaa Ser Ser
1 5 10

<210> SEQ ID NO 13
<211> LENGTH: 11
<212> TYPE: PRT
<213> ORGANISM: Artificial Sequence
<220> FEATURE:
<223> OTHER INFORMATION: self-assembling peptide

<400> SEQUENCE: 13

Ser Ser Arg Phe Glu Trp Glu Phe Glu Ser Ser
1 5 10

<210> SEQ ID NO 14
<211> LENGTH: 11
<212> TYPE: PRT
<213> ORGANISM: Artificial Sequence
<220> FEATURE:
<223> OTHER INFORMATION: self-assembling peptide
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (7)..(7)
<223> OTHER INFORMATION: Orn

<400> SEQUENCE: 14

Ser Ser Arg Phe Xaa Trp Xaa Phe Glu Ser Ser
1 5 10

<210> SEQ ID NO 15
<211> LENGTH: 11
<212> TYPE: PRT
<213> ORGANISM: Artificial Sequence
<220> FEATURE:
<223> OTHER INFORMATION: self-assembling peptide
<220> FEATURE:
<221> NAME/KEY: MOD_RES
<222> LOCATION: (3)..(3)
<223> OTHER INFORMATION: Orn
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (7)..(7)
<223> OTHER INFORMATION: Orn
<220> FEATURE:

-continued

<221> NAME/KEY: MOD_RES
<222> LOCATION: (9)..(9)
<223> OTHER INFORMATION: Orn

<400> SEQUENCE: 15

Gln Gln Xaa Phe Xaa Trp Xaa Phe Xaa Gln Gln
1               5                   10

<210> SEQ ID NO 16
<211> LENGTH: 11
<212> TYPE: PRT
<213> ORGANISM: Artificial Sequence
<220> FEATURE:
<223> OTHER INFORMATION: self-assembling peptide

<400> SEQUENCE: 16

Asn Asn Arg Phe Glu Trp Glu Phe Glu Asn Asn
1               5                   10

<210> SEQ ID NO 17
<211> LENGTH: 11
<212> TYPE: PRT
<213> ORGANISM: Artificial Sequence
<220> FEATURE:
<223> OTHER INFORMATION: self-assembling peptide
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (7)..(7)
<223> OTHER INFORMATION: Orn

<400> SEQUENCE: 17

Asn Asn Arg Phe Xaa Trp Xaa Phe Glu Asn Asn
1               5                   10

<210> SEQ ID NO 18
<211> LENGTH: 11
<212> TYPE: PRT
<213> ORGANISM: Artificial Sequence
<220> FEATURE:
<223> OTHER INFORMATION: self-assembling peptide

<400> SEQUENCE: 18

Thr Thr Arg Phe Glu Trp Glu Phe Glu Thr Thr
1               5                   10

<210> SEQ ID NO 19
<211> LENGTH: 11
<212> TYPE: PRT
<213> ORGANISM: Artificial Sequence
<220> FEATURE:
<223> OTHER INFORMATION: self-assembling peptide
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (7)..(7)
<223> OTHER INFORMATION: Orn

<400> SEQUENCE: 19

Thr Thr Arg Phe Xaa Trp Xaa Phe Glu Thr Thr
1               5                   10

<210> SEQ ID NO 20

-continued

<211> LENGTH: 11
<212> TYPE: PRT
<213> ORGANISM: Artificial Sequence
<220> FEATURE:
<223> OTHER INFORMATION: self-assembling peptide P11-20

<400> SEQUENCE: 20

Gln Gln Arg Gln Glu Gln Glu Gln Glu Gln Gln
1 5 10

<210> SEQ ID NO 21
<211> LENGTH: 5
<212> TYPE: PRT
<213> ORGANISM: Artificial Sequence
<220> FEATURE:
<223> OTHER INFORMATION: designed self-assembling peptide, consensus sequence 1
<220> FEATURE:
<221> NAME/KEY: VARIANT
<222> LOCATION: 1..1
<223> OTHER INFORMATION: amino acid with acidic or basic side chain
<220> FEATURE:
<221> NAME/KEY: VARIANT
<222> LOCATION: 2..2
<223> OTHER INFORMATION: amino acid with hydrophobic or polar side chain that is selected from the group consisting of alanine, valine, isoleucine, leucine, methionine, phenylalanine, tyrosine, tryptophan and glutamine
<220> FEATURE:
<221> NAME/KEY: VARIANT
<222> LOCATION: 3..3
<223> OTHER INFORMATION: amino acid with acidic or basic side chain
<220> FEATURE:
<221> NAME/KEY: VARIANT
<222> LOCATION: 4..4
<223> OTHER INFORMATION: amino acid with hydrophobic or polar side chain that is selected from the group consisting of alanine, valine, isoleucine, leucine, methionine, phenylalanine, tyrosine, tryptophan and glutamine
<220> FEATURE:
<221> NAME/KEY: VARIANT
<222> LOCATION: 5..5
<223> OTHER INFORMATION: amino acid with acidic or basic side chain

<400> SEQUENCE: 21

Xaa Xaa Xaa Xaa Xaa
1 5

<210> SEQ ID NO 22
<211> LENGTH: 5
<212> TYPE: PRT
<213> ORGANISM: Artificial Sequence
<220> FEATURE:
<223> OTHER INFORMATION: designed self-assembling peptide assembling at a pH below 7.5
<220> FEATURE:
<221> NAME/KEY: VARIANT
<222> LOCATION: 1..1
<223> OTHER INFORMATION: amino acid with acidic side chain
<220> FEATURE:
<221> NAME/KEY: VARIANT
<222> LOCATION: 2..2
<223> OTHER INFORMATION: amino acid with hydrophobic or polar side chain that is selected from the group consisting of alanine, valine, isoleucine, leucine, methionine, phenylalanine, tyrosine, tryptophan and glutamine
<220> FEATURE:
<221> NAME/KEY: VARIANT
<222> LOCATION: 3..3
<223> OTHER INFORMATION: amino acid with acidic side chain
<220> FEATURE:
<221> NAME/KEY: VARIANT
<222> LOCATION: 4..4
<223> OTHER INFORMATION: amino acid with hydrophobic or polar side chain that is selected from the group consisting of alanine, valine, -continued

```
      isoleucine, leucine, methionine, phenylalanine, tyrosine,
      tryptophan and glutamine
<220> FEATURE:
<221> NAME/KEY: VARIANT
<222> LOCATION: 5..5
<223> OTHER INFORMATION: amino acid with acidic side chain

<400> SEQUENCE: 22

Xaa Xaa Xaa Xaa Xaa
1               5


<210> SEQ ID NO 23
<211> LENGTH: 5
<212> TYPE: PRT
<213> ORGANISM: Artificial Sequence
<220> FEATURE:
<223> OTHER INFORMATION: designed self-assembling peptide
<220> FEATURE:
<221> NAME/KEY: VARIANT
<222> LOCATION: 1..1
<223> OTHER INFORMATION: amino acid with acidic side chain
<220> FEATURE:
<221> NAME/KEY: VARIANT
<222> LOCATION: 2..2
<223> OTHER INFORMATION: amino acid with hydrophobic side chain that is
      selected from the group consisting of alanine, valine, isoleucine,
      leucine, methionine, phenylalanine, tyrosine and tryptophan
<220> FEATURE:
<221> NAME/KEY: VARIANT
<222> LOCATION: 3..3
<223> OTHER INFORMATION: amino acid with acidic side chain
<220> FEATURE:
<221> NAME/KEY: VARIANT
<222> LOCATION: 4..4
<223> OTHER INFORMATION: amino acid with hydrophobic side chain that is
      selected from the group consisting of alanine, valine, isoleucine,
      leucine, methionine, phenylalanine, tyrosine and tryptophan
<220> FEATURE:
<221> NAME/KEY: VARIANT
<222> LOCATION: 5..5
<223> OTHER INFORMATION: amino acid with acidic side chain

<400> SEQUENCE: 23

Xaa Xaa Xaa Xaa Xaa
1               5


<210> SEQ ID NO 24
<211> LENGTH: 5
<212> TYPE: PRT
<213> ORGANISM: Artificial Sequence
<220> FEATURE:
<223> OTHER INFORMATION: designed self-assembling peptide
<220> FEATURE:
<221> NAME/KEY: VARIANT
<222> LOCATION: 2..2
<223> OTHER INFORMATION: amino acid with hydrophobic side chain that is
      selected from the group consisting of alanine, valine, isoleucine,
      leucine, methionine, phenylalanine, tyrosine and tryptophan
<220> FEATURE:
<221> NAME/KEY: VARIANT
<222> LOCATION: 4..4
<223> OTHER INFORMATION: amino acid with hydrophobic side chain that is
      selected from the group consisting of alanine, valine, isoleucine,
      leucine, methionine, phenylalanine, tyrosine and tryptophan

<400> SEQUENCE: 24

Glu Xaa Glu Xaa Glu
1               5


<210> SEQ ID NO 25
<211> LENGTH: 5
<212> TYPE: PRT
<213> ORGANISM: Artificial Sequence
```

-continued

```
<220> FEATURE:
<223> OTHER INFORMATION: designed self-assembling peptide
<220> FEATURE:
<221> NAME/KEY: VARIANT
<222> LOCATION: 2..2
<223> OTHER INFORMATION: amino acid with hydrophobic side chain that is
      selected from the group consisting of alanine, valine, isoleucine,
      leucine, methionine, phenylalanine, tyrosine and tryptophan
<220> FEATURE:
<221> NAME/KEY: VARIANT
<222> LOCATION: 4..4
<223> OTHER INFORMATION: amino acid with hydrophobic side chain that is
      selected from the group consisting of alanine, valine, isoleucine,
      leucine, methionine, phenylalanine, tyrosine and tryptophan

<400> SEQUENCE: 25

Asp Xaa Asp Xaa Asp
1               5


<210> SEQ ID NO 26
<211> LENGTH: 5
<212> TYPE: PRT
<213> ORGANISM: Artificial Sequence
<220> FEATURE:
<223> OTHER INFORMATION: designed self-assembling peptide

<400> SEQUENCE: 26

Glu Gln Glu Gln Glu
1               5
```